US010501453B2

(12) United States Patent
Dahl et al.

(10) Patent No.: US 10,501,453 B2
(45) Date of Patent: *Dec. 10, 2019

(54) BENZOTHIAZOLE OR BENZOXAZOLE COMPOUNDS AS SUMO ACTIVATORS

(71) Applicant: Icahn School of Medicine at Mount Sinai, New York, NY (US)

(72) Inventors: Russell Dahl, Carlsbad, CA (US); Ah Young Lee, New York, NY (US); Changwon Kho, New York, NY (US); Roger J. Hajjar, Tenafly, NJ (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/826,238

(22) Filed: Nov. 29, 2017

(65) Prior Publication Data

US 2018/0127407 A1    May 10, 2018

Related U.S. Application Data

(63) Continuation of application No. 14/424,289, filed as application No. PCT/US2013/057264 on Aug. 29, 2013, now Pat. No. 9,845,320.

(60) Provisional application No. 61/694,667, filed on Aug. 29, 2012.

(51) Int. Cl.
| | |
|---|---|
| C07D 417/12 | (2006.01) |
| C07D 413/12 | (2006.01) |
| A61K 31/428 | (2006.01) |
| A61K 31/4245 | (2006.01) |
| A61K 31/433 | (2006.01) |
| C07D 413/04 | (2006.01) |
| A61K 48/00 | (2006.01) |

(52) U.S. Cl.
CPC .......... *C07D 417/12* (2013.01); *A61K 31/428* (2013.01); *A61K 31/4245* (2013.01); *A61K 31/433* (2013.01); *A61K 48/00* (2013.01); *C07D 413/04* (2013.01); *C07D 413/12* (2013.01)

(58) Field of Classification Search
CPC ............................. C07D 417/12; C07D 413/12
See application file for complete search history.

(56) References Cited

U.S. PATENT DOCUMENTS

| | | | | |
|---|---|---|---|---|
| 6,080,772 A | * | 6/2000 | Tang ................. | C07D 277/58 514/370 |
| 9,845,320 B2 | * | 12/2017 | Dahl ................. | A61K 31/4245 |
| 2009/0069288 A1 | | 3/2009 | Breinlinger et al. | |
| 2011/0256101 A1 | | 10/2011 | Hajjar et al. | |
| 2012/0101123 A1 | | 4/2012 | Li et al. | |

FOREIGN PATENT DOCUMENTS

WO    2011/069647    6/2011

OTHER PUBLICATIONS

Patani et al. Chem. Rev. 1996, 96, 3147-3176 (Year: 1996).*
National Center for Biotechnology Information. PubChem BioAssay Database; AID=430, https://pubchem.ncbi.nlm.nih.gov/bioassay/430 (accessed Apr. 29, 2017, deposit date Jun. 14, 2006) (Year: 2006).*
National Center for Biotechnology Information. PubChem Compound Database; CID=3236395, https://pubchem.ncbi.nlm.nih.gov/compound/3236395 (accessed Jul. 11, 2016, create date Aug. 16, 2005) (Year: 2005).*
National Center for Biotechnology Information. PubChem BioAssay Database; AID=430, https://pubchem.ncbi.nlm.nih.gov/bioassay/430 (accessed Jun. 12, 2018, deposit date Jun. 14, 2006) (Year: 2006).*
National Center for Biotechnology Information. PubChem Compound Database; CID=3243386, https://pubchem.ncbi.nlm.nih.gov/compound/3243386 (create date Aug. 16, 2005, accessed Jun. 12, 2018) (Year: 2005).*
National Center for Biotechnology Information. PubChem BioAssay Database; AID=485313, https://pubchem.ncbi.nlm.nih.gov/bioassay/485313 (deposit date Sep. 29, 2010, accessed Jun. 12, 2018) (Year: 2010).*
National Center for Biotechnology Information. PubChem BioAssay Database; AID=1835, https://pubchem.ncbi.nlm.nih.gov/bioassay/1835 (accessed Dec. 26, 2018; version Mar. 25, 2010) (Year: 2010).*
National Center for Biotechnology Information. PubChem Compound Database; CID=7109931, https://pubchem.ncbi.nlm.nih.gov/compound/7109931 (accessed Dec. 26, 2018; create date Jul. 29, 2006) (Year: 2006).*
PubChem CID-3236395 (Create Date: Aug. 16, 2005) p. 1, Fig.
Amir et al., "Synthesis of pharmaceutically important 1,3,4-thiadiazole and imidazolinone derivatives as antimicrobials," Indian Journal of Chemistry, vol. 48B, Sep. 2009, pp. 1288-1293; p. 1283, Scheme 1, Table 1; p. 1290, Table II.
International Search Report and Written Opinion issued in PCT/US2013/057264 dated Jan. 7, 2014.
Partial Supplementary European Search Report in European Application No. 13834186.2, dated Jul. 4, 2016, 7 pages.
Kho et al., "SUMOylation of SERCA2a improves cardiac contractile function," Journal of Molecular and Cellular Cardiology, Mar. 2010, 48: S7.
Jeong et al., "Effects of SUMO1 cardiac gene transfer of SERCA2a activity in rodent models of heart failure," Journal of Molecular and Cellular Cardiology, Mar. 2010, 48: S9.
Kho et al., "SUMO1-dependent modulation, of SERCA2a in heart failure," Nature, Sep. 2011, 477: 601-605.

(Continued)

*Primary Examiner* — Matthew P Coughlin
(74) *Attorney, Agent, or Firm* — Fish & Richardson P.C.

(57) ABSTRACT

Provided are SUMO activators, which can enhance SUMOylation of SERCA2a, which are useful in the treatment of heart failure, cardiovascular diseases, cancer, neurodegenerative disorders, viral infection, bacterial infection, liver disease, inflammation, and other diseases.

16 Claims, 28 Drawing Sheets

(56) References Cited

OTHER PUBLICATIONS

Giliani et al., "Synthesis and in vitro antimicrobial activity of novel N-(6-chlorobenzo[d] thiazol-2-yl) hydrazine carboxamide derivatives of benzothiazole class", Journal of Enzyme Inhibition and Medicinal Chemistry, Jun. 2011, 26: 332-340.

Lauer-Fields et al., "High throughput screening of potentially selective MMP-13 exosite inhibitors utilizing a triple-helical FRET substrate," Bioorganic & Medicinal Chemistry, Feb. 2009, 17: 990-1005.

Bettermann et al., "SUMOylation in carcinogenesis," Cancer Letters, Mar. 2012, 316: 113-125.

Steffan et al., "SUMO modification of Huntingtin and Huntington's disease pathology," Science, Apr. 2004, 304: 100-104.

Dorval and Fraser, "Small ubiquitin-like modifier (SUMO) modification of natively unfolded proteins tau and a-synuclein," J. Biol. Chem., Apr. 2006, 281: 9919-9924.

Zhang and Sarge, "Sumoylation of amyloid precursor protein negatively regulates Aβ aggregate levels," Biochem. Biophys. Res. Commun., 2008, 374: 673-678.

Fei et al., "SUMO-1 modification increases human SOD1 stability and aggregation," Biochem Biophys. Res. Commun., 2006, 347: 406-412.

Békés and Drag, "Trojan horse strategies used by pathogens to influence the small ubiquitin-like modifier (SUMO) system of host eukaryotic cells," J Innate Immun., 2012, 4: 159-67.

Guo et al., "Overexpression of SUMO-1 in hepatocellular carcinoma: a latent target for diagnosis and therapy of hepatoma," J Cancer Res Clin Oncol., Mar. 2011, 137: 533-41.

Pascual et al., "A SUMOylation-dependent pathway mediates transrepression of inflammatory response genes by PPAR-γ," Nature, Sep. 2005, 437: 759-63.

\* cited by examiner

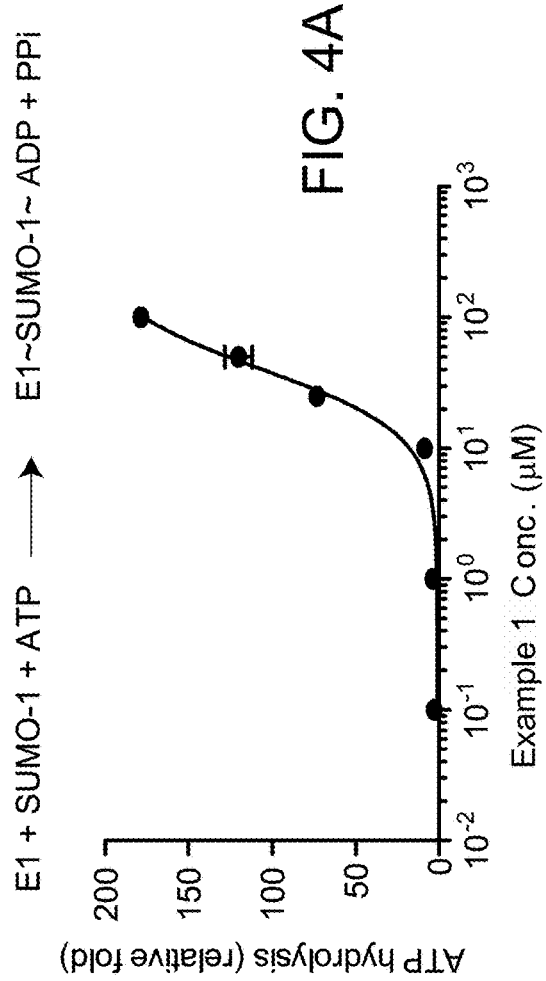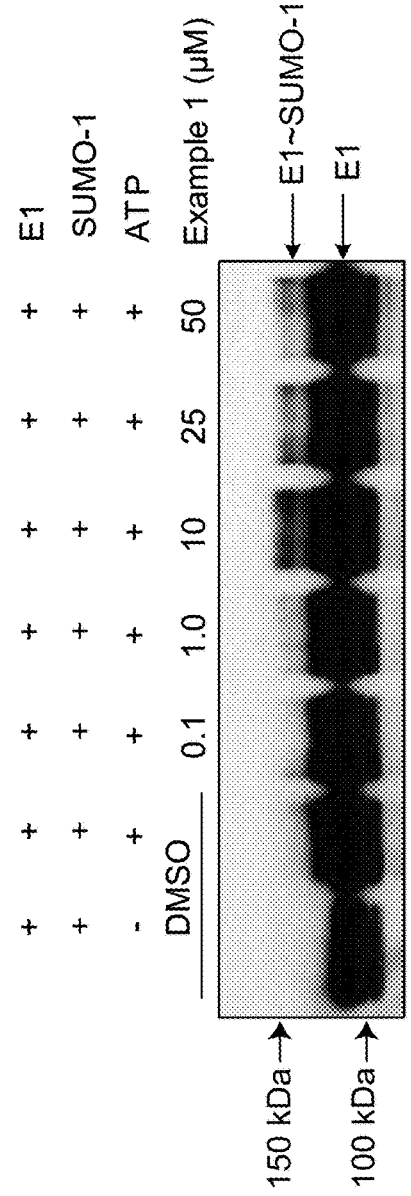

| | EC50 (µM) |
|---|---|
| PPi | 40.47 ± 4.40 |
| E1~SUMO-1 | 1.85 ± 0.96 |
| E2~SUMO-1 | 10.17 ± 0.28 |

BENZOTHIAZOLE OR BENZOXAZOLE COMPOUNDS AS SUMO ACTIVATORS

CROSS-REFERENCE TO RELATED APPLICATION

This application is a continuation of U.S. application Ser. No. 14/424,289 filed Feb. 26, 2015, which is a § 371 National Stage Application of PCT/US2013/057264, filed Aug. 29, 2013, which claims priority to U.S. provisional application No. 61/694,667 filed Aug. 29, 2012, each of which is incorporated herein by reference in its entirety.

TECHNICAL FIELD

The present application relates to SUMO activators, which can enhance SUMOylation of SERCA2a, which are useful in the treatment of heart failure, cardiovascular diseases, cancer, neurodegenerative disorders, viral infection, bacterial infection, liver disease, inflammation, and other diseases.

BACKGROUND

Heart failure (HF) remains a leading cause of death in Western countries and the development of new therapeutic agents for HF has been challenged. The recent major advances in the understanding of molecular signaling in the cardiac myocytes under the pathological stress has suggested the way for different approaches to treating heart disease, in particular to regulate intrinsic targets on the intracellular side. The calcium-transporting ATPase ATP2A2 (SERCA2a) is ATPase responsible for $Ca^{2+}$ re-uptake during excitation-contraction coupling. A characteristic of heart failure is impaired $Ca^{2+}$ uptake resulting from decreased expression and reduced activity of SERCA2a. To this end, restoration of SERCA2a expression by gene transfer can be effective in improving cardiac function in animal models and heart-failure patients. It was found that the levels and activity of SERCA2a in cardiac myocytes are modulated by small ubiquitin-like modifier type 1 (SUMO I)-mediated unique post-translational modification (PTM), named SUMOylation (Kho C, Lee A, Jeong D, Oh J G Chaanine A H, Kizana E, Park W J, Hajjar R J, "SUMO1-dependent modulation of SERCA2a in heart failure", Nature 2011 Sep. 7; 477(7366):601-5). SERCA2a is SUMOYLated by SUMO1 at two specific sites Lysine 480 and 585. The levels of SUMO1 and the SUMOylation of SERCA2a itself were greatly reduced in failing hearts. SUMO1 restitution by adeno-associated-virus-mediated gene delivery maintained the protein abundance of SERCA2a and markedly improved cardiac function in mice with heart failure. This effect was comparable to SERCA2A gene delivery. Since it has been shown that SUMO1 enhances the stability and the ATPase activity of SERCA2a, its decrease causes further dysfunction of SERCA2a and further worsening of dysfunction. Further, gain of function experiments by transgenesis and gene therapy showed that SUMO1 gene therapy rescues contractile function and improves mortality in models of heart failure. To this end, there is a need to develop new small molecules that increase SERCA2a SUMOylation, which are are useful for treating HF.

Further, induction of SUMOylation has also been implicated in the treatment of cancer (Kira Bettermann, Martin Benesch, Serge Weis, Johannes Haybaeck. SUMOylation in carcinogenesis. *Cancer Letters* (2012) 316, 113-125), neurodegenerative disorders such as Huntington's disease (Steffan, J. S. et al. SUMO modification of Huntingtin and Huntington's disease pathology. *Science* (2004) 304, 100-104), Parkinson's disease (Dorval, V., Fraser, P. E. Small ubiquitin-like modifier (SUMO) modification of natively unfolded proteins tau and a-synuclein. *J. Biol. Chem.* (2006) 281, 9919-9924), Alzheimer's disease (Zhang, Y Q. and Sarge, K. D. Sumoylation of amyloid precursor protein negatively regulates Ab aggregate levels. (2008) *Biochem. Biophys. Res. Commun.* 374, 673-678), and amyotrophic lateral sclerosis (ALS) (Fei, E. et al. SUMO-1 modification increases human SOD1 stability and aggregation. *Biochem. Biophys. Res. Commun.* (2006) 347, 406-412), viral and bacterial infection (Békés M, Drag M. Trojan horse strategies used by pathogens to influence the small ubiquitin-like modifier (SUMO) system of host eukaryotic cells. *J Innate Immun.* (2012) 4, 159-67), liver disease (Guo W H, Yuan L H, Xiao Z H, Liu D, Zhang J X. Overexpression of SUMO-1 in hepatocellular carcinoma: a latent target for diagnosis and therapy of hepatoma. *J Cancer Res Clin Oncol.* (2011) 137, 533-41), and inflammation (Pascual G, Fong A L, Ogawa S, Gamliel A, Li A C, Perissi V, Rose D W, Willson T M, Rosenfeld M G, Glass C K. A SUMOylation-dependent pathway mediates transrepression of inflammatory response genes by PPAR-gamma. *Nature* (2005) 437, 759-63).

To this end, there is a need to develop new small molecules that increase SERCA2a SUMOylation, which are useful for treating HF. This application addresses this need and others.

SUMMARY

The present application provides, inter alia, a method of treating heart failure, cardiac hypertrophy, myocarditis, myocardial infarction, ischemia, cardiac arrhythmias, vascular rhexis, cardiac arrhythmia, valvulopathy, diastolic dysfunction, hypertension, cancer, neurodegenerative disorders, viral infection, bacterial infection, liver disease, or inflammation in a patient in need thereof, comprising administering to said patient a therapeutically effective amount of a compound of Formula II:

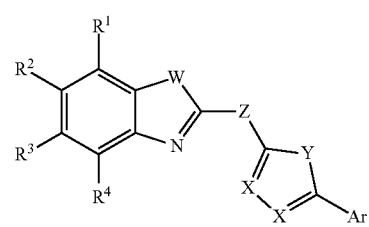

or a pharmaceutically acceptable salt thereof; wherein:
Ar is aryl or heteroaryl, each of which is optionally substituted with 1, 2, 3, 4, 5, or 6 independently selected $R^{1a}$ groups;
W is S or O;
Y is S or O;
each X is independently CH or N;
Z is O, S, or $NR^A$;
$NR^A$ is H or $C_{1-4}$ alkyl;
$R^1$, $R^2$, $R^3$, and $R^4$ are each independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino; and each $R^{1a}$ is independently selected from halo, CN, nitro, hydroxy, $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino; or two adjacent $R^{1a}$ taken together with the atoms to which they are attached can form a 3-7 membered carbocyclic or 4-6 membered heterocyclic ring, each of which is optionally substituted with 1, 2, 3, or 4 $C_{1-3}$ alkyl groups.

In some embodiments, heart failure is selected from congestive heart failure (CHF), chronic heart failure, and ischemic heart failure.

The present invention further provides a method of treating heart failure, cardiac hypertrophy, myocarditis, myocardial infarction, ischemia, cardiac arrhythmias, vascular rhexis, cardiac arrhythmia, valvulopathy, diastolic dysfunction, hypertension, cancer, neurodegenerative disorders, viral infection, bacterial infection, liver disease, or inflammation in a patient in need thereof, comprising administering to said patient a therapeutically effective amount of a compound of a compound of Formula I:

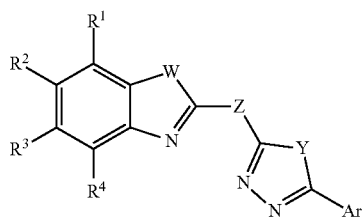

I or a pharmaceutically acceptable salt thereof; wherein:
Ar is aryl or heteroaryl, each of which is optionally substituted with 1, 2, 3, 4, 5, or 6 independently selected $R^{1a}$ groups;
W is S or O;
Y is S or O;
Z is O, S, or $NR^A$;
$NR^A$ is H or $C_{1-4}$ alkyl;

$R^1$, $R^2$, $R^3$, and $R^4$ are each independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino; and each $R^{1a}$ is independently selected from halo, CN, nitro, hydroxy, $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino.

In some embodiments, Ar is phenyl, which is optionally substituted by 1, 2, 3, 4, or 5 independently selected $R^{1a}$ groups.

In some embodiments, each $R^{1a}$ is independently selected from halo, CN, hydroxy, $C_{1-6}$ alkyl, $C_{1-6}$ haloalkyl, $C_{1-6}$ alkoxy, and $C_{1-6}$ haloalkoxy. In some embodiments, each $R^{1a}$ is independently selected from hydrogen and $C_{1-6}$ alkoxy.

In some embodiments, W is S.
In some embodiments, Y is O.
In some embodiments, Z is NH.
In some embodiments, $R^1$, $R^2$, $R^3$, and $R^4$ are independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, and di-$C_{1-4}$-alkylamino. In some embodiments, $R^1$, $R^2$, $R^3$, and $R^4$ are independently selected from hydrogen, halo, and $C_{1-6}$ alkoxy. In some embodiments, at least three of $R^1$, $R^2$, $R^3$, and $R^4$ are hydrogen. In some embodiments, $R^1$, $R^2$, $R^3$, and $R^4$ are hydrogen.

In some embodiments, the compound is a compound of Formula Ia:

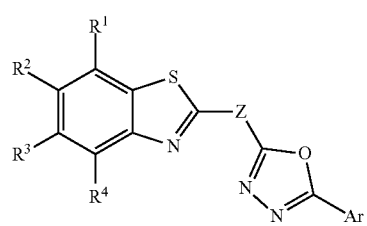

Ia or a pharmaceutically acceptable salt thereof.

In some embodiments, the compound is a compound of Formula Ib:

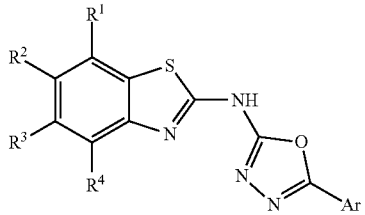

Ib or a pharmaceutically acceptable salt thereof.

In some embodiments, the compound is a compound of Formula Ic:

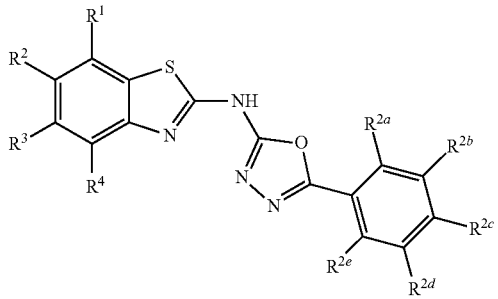

Ic or a pharmaceutically acceptable salt thereof; wherein:

$R^{2a}$, $R^{2b}$, $R^{2c}$, $R^{2d}$, and $R^{2e}$ are each independently selected from hydrogen, halo, CN, nitro, hydroxy, $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino.

In some embodiments, $R^1$, $R^2$, $R^3$, $R^4$, $R^{2a}$, $R^{2b}$, $R^{2c}$, $R^{2d}$, and $R^{2e}$ are each independently selected from hydrogen, halo, CN, hydroxy, $C_{1-6}$ alkyl, $C_{1-6}$ haloalkyl, $C_{1-6}$ alkoxy, and $C_{1-6}$ haloalkoxy.

In some embodiments, each X is CH.

In some embodiments, the compound is a compound of Formula IIa:

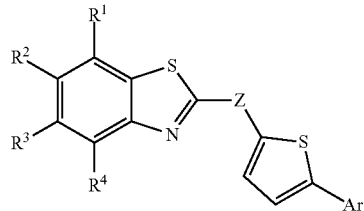

IIa or a pharmaceutically acceptable salt thereof.

In some embodiments, the compound is a compound of Formula IIb:

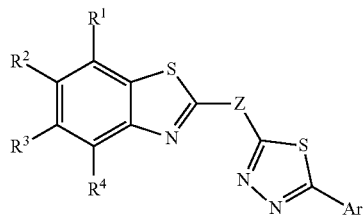

IIb or a pharmaceutically acceptable salt thereof.

In some embodiments, the compound is a compound of Formula IIc:

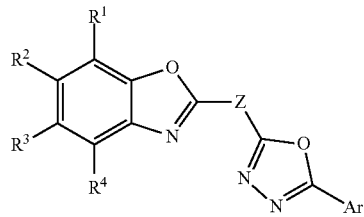

IIc or a pharmaceutically acceptable salt thereof.

In some embodiments, the compound is a compound selected from the compounds of Table 1a, Table 1b, Table 1c, and Table 1d; or a pharmaceutically acceptable salt thereof.

Non-limiting examples of compounds of Formula II include:

5-(4-fluorophenyl)-N-(4-methoxybenzo[d]thiazol-2-yl)-1,3, 4-oxadiazol-2-amine;

5-(2,4-dimethoxyphenyl)-N-(4-methoxybenzo[d]thiazol-2-yl)-1,3,4-oxadiazol-2-amine;

N-(4-fluorobenzo[d]thiazol-2-yl)-5-phenyl-1,3,4-oxadiazol-2-amine;

N-(6-methoxybenzo[d]thiazol-2-yl)-5-(2-methoxyphenyl)-1,3,4-oxadiazol-2-amine;

N-(6-methoxybenzo[d]thiazol-2-yl)-5-(4-methoxyphenyl)-1,3,4-oxadiazol-2-amine;

5-(4-chlorophenyl)-N-(6-methoxybenzo[d]thiazol-2-yl)-1, 3,4-oxadiazol-2-amine;

5-(2-chlorophenyl)-N-(6-fluorobenzo[d]thiazol-2-yl)-1,3,4-oxadiazol-2-amine;

N-(6-fluorobenzo[d]thiazol-2-yl)-5-(4-fluorophenyl)-1,3,4-oxadiazol-2-amine;

N-(6-fluorobenzo[d]thiazol-2-yl)-5-(3-methoxyphenyl)-1,3, 4-oxadiazol-2-amine;

N-(6-fluorobenzo[d]thiazol-2-yl)-5-(4-methoxyphenyl)-1,3,4-oxadiazol-2-amine;
N-(5-methoxybenzo[d]thiazol-2-yl)-5-(3-methoxyphenyl)-1,3,4-oxadiazol-2-amine;
N-(5-methoxybenzo[d]thiazol-2-yl)-5-(4-methoxyphenyl)-1,3,4-oxadiazol-2-amine;
N-(5,6-dimethoxybenzo[d]thiazol-2-yl)-5-(4-methoxyphenyl)-1,3,4-oxadiazol-2-amine;
5-(4-methoxyphenyl)-N-(6-(methylthio)benzo[d]thiazol-2-yl)-1,3,4-oxadiazol-2-amine;
N-(4-methoxybenzo[d]thiazol-2-yl)-5-(4-methoxyphenyl)-1,3,4-oxadiazol-2-amine;
N-(4-fluorobenzo[d]thiazol-2-yl)-5-(4-fluorophenyl)-1,3,4-oxadiazol-2-amine;
N-(4-fluorobenzo[d]thiazol-2-yl)-5-(3-methoxyphenyl)-1,3,4-oxadiazol-2-amine; and
N-(4-fluorobenzo[d]thiazol-2-yl)-5-(4-methoxyphenyl)-1,3,4-oxadiazol-2-amine, or a pharmaceutically acceptable salt thereof.

In some embodiments, the compound is selected from:
N-(4-methoxybenzo[d]thiazol-2-yl)-5-(4-methoxyphenyl)-1,3,4-oxadiazol-2-amine;
N-(4-fluorobenzo[d]thiazol-2-yl)-5-(4-fluorophenyl)-1,3,4-oxadiazol-2-amine;
N-(4-fluorobenzo[d]thiazol-2-yl)-5-(3-methoxyphenyl)-1,3,4-oxadiazol-2-amine; and
N-(4-fluorobenzo[d]thiazol-2-yl)-5-(4-methoxyphenyl)-1,3,4-oxadiazol-2-amine, or a pharmaceutically acceptable salt thereof.

The present application also provides a method which further comprises administering to the patient an adeno-associated vector (AAV) comprising SERCA2a.

The present application further provides a method of activating SUMO1, comprising contacting comprising contacting a cell with a compound, salt, or composition described herein, in an amount effective to activate SUMO1.

The present application further provides a compound or salt as described herein for use in any of the methods described herein.

The present application further provides use of a compound or salt as described herein for manufacture of a medicament for use in any of the method described herein.

The present application further provides a pharmaceutical composition comprising any of the compounds described herein, or a pharmaceutically acceptable salt thereof, and at least one pharmaceutically acceptable carrier. The present application further provides a compound, which is N-(4-methoxybenzo[d]thiazol-2-yl)-5-(4-methoxyphenyl)-1,3,4-oxadiazol-2-amine, or a pharmaceutically acceptable salt thereof.

DESCRIPTION OF DRAWINGS

FIG. 1A depicts intracellular fluorescence measurements for DMSO control versus Example 1 in HEK-293 cells expressing YFP-SUMO1 and pcDNA3.0-SERCA2a.

FIG. 4A depicts a plot of ATP hydrolysis vs. Example 1 concentration in the presence of SUMO-1.

FIG. 4B depicts a blot of concentrations of Example 1 and a SUMO-1 and SUMO E1 enzyme

FIG. 14 depicts the effects of Examples 1-4 on YFP-SUMO1 accumulation in the nucleus and SUMOylation of SERCA2a.

DETAILED DESCRIPTION

Figure 1A:
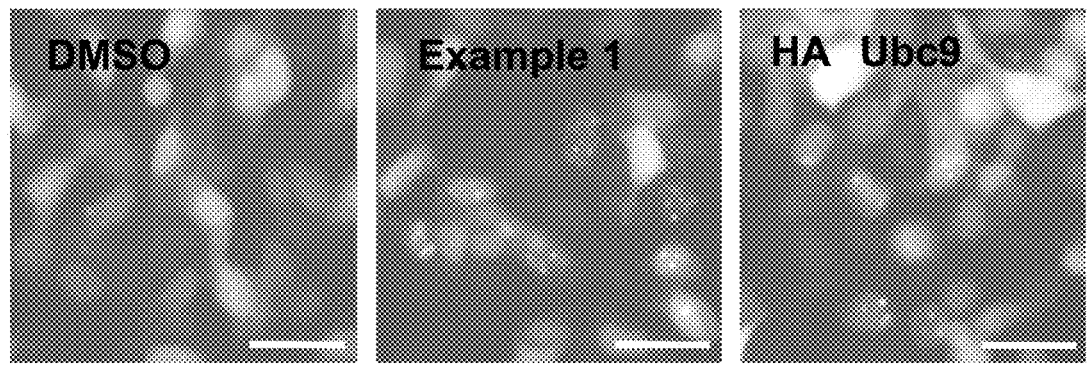

The present application provides, inter alia, a method of treating heart failure, cardiac hypertrophy, myocarditis, myocardial infarction, ischemia, cardiac arrhythmias, vascular rhexis, cardiac arrhythmia, valvulopathy, diastolic dysfunction, hypertension, cancer, neurodegenerative disorders, viral infection, bacterial infection, liver disease, or inflammation in a patient in need thereof, comprising administering to said patient a therapeutically effective amount of a compound of Formula II:

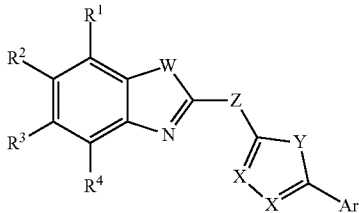

or a pharmaceutically acceptable salt thereof; wherein:
Ar is aryl or heteroaryl, each of which is optionally substituted with 1, 2, 3, 4, 5, or 6 independently selected $R^{1a}$ groups;
W is S or O;
Y is S or O;
each X is independently CH or N;
Z is O, S, or $NR^A$;
$NR^A$ is H or $C_{1-4}$ alkyl;
$R^1$, $R^2$, $R^3$, and $R^4$ are each independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino; and
each $R^{1a}$ is independently selected from halo, CN, nitro, hydroxy, $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino; or
two adjacent $R^{1a}$ taken together with the atoms to which they are attached can form a 3-7 membered carbocyclic or 4-6 membered heterocyclic ring, each of which is optionally substituted with 1, 2, 3, or 4 $C_{1-3}$ alkyl groups.

In some embodiments, the present application provides, a method of treating heart failure, cardiac hypertrophy, myocarditis, myocardial infarction, ischemia, cardiac arrhythmias, vascular rhexis, cardiac arrhythmia, valvulopathy, diastolic dysfunction, hypertension, cancer, neurodegenerative disorders, viral infection, bacterial infection, liver disease, or inflammation in a patient in need thereof, comprising administering to said patient a therapeutically effective amount of a compound of Formula I:

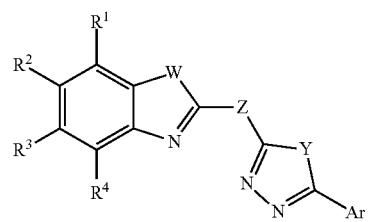

or a pharmaceutically acceptable salt thereof; wherein:
Ar is aryl or heteroaryl, each of which is optionally substituted with 1, 2, 3, 4, 5, or 6 independently selected $R^{1a}$ groups;
W is S or O;
Y is S or O;
Z is O, S, or $NR^A$;
$NR^A$ is H or $C_{1-4}$ alkyl;
$R^1$, $R^2$, $R^3$, and $R^4$ are each independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino; and
each $R^{1a}$ is independently selected from halo, CN, nitro, hydroxy, $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino.

In some embodiments, the heart failure is selected from congestive heart failure (CHF), chronic heart failure, and ischemic heart failure.

Cancers include, but are not limited to, solid tumors such as breast, ovarian, prostate, lung, kidney, gastric, colon, testicular, head and neck, pancreas, brain, melanoma, and other tumors of tissue organs and cancers of the blood cells, such as lymphomas and leukemias, including acute myelogenous leukemia, chronic lymphocytic leukemia, T cell lymphocytic leukemia, and B cell lymphomas.

Inflammatory disorders include, but are not limited to, transplant rejection, including skin graft rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure, brain and spinal cord trauma, and cancer. There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy.

Neurodegenerative disorders include, but are not limited to Huntington's disease, Parkinson's disease, Alzheimer's disease, and amyotrophic lateral sclerosis (ALS).

Viral infections, include but are not limited to, infections by a hepatitis virus (e.g., hepatitis B or C), human immunodeficiency virus (HIV), rhinovirus, herpes-zoster virus (VZV), herpes simplex virus (e.g., HSV-1 or HSV-2), cytomegalovirus (CMV), vaccinia virus, influenza virus, encephalitis virus, hantavirus, arbovirus, West Nile virus, human papilloma virus (HPV), Epstein-Ban virus, and respiratory syncytial virus.

Liver diseases include, but are not limited to liver cirrhosis, alcoholic liver cirrhosis, fatty liver, toxipathic liver diseases, and acute and chronic hepatitis.

In some embodiments, Ar is phenyl, which is optionally substituted by 1, 2, 3, 4, or 5 independently selected $R^{1a}$ groups.

In some embodiments, each $R^{1a}$ is independently selected from halo, CN, hydroxy, $C_{1-6}$ alkyl, $C_{1-6}$ haloalkyl, $C_{1-6}$ alkoxy, and $C_{1-6}$ haloalkoxy.

In some embodiments, each $R^{1a}$ is independently selected from hydrogen and $C_{1-6}$ alkoxy.

In some embodiments, W is S.
In some embodiments, Y is O.
In some embodiments, Z is NH.
In some embodiments, $R^1$, $R^2$, $R^3$, and $R^4$ are independently selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, and di-$C_{1-4}$-alkylamino.

In some embodiments, $R^1$, $R^2$, $R^3$, and $R^4$ are independently selected from hydrogen, halo, and $C_{1-6}$ alkoxy.

In some embodiments, at least three of $R^1$, $R^2$, $R^3$, and $R^4$ are hydrogen.

In some embodiments, $R^1$, $R^2$, $R^3$, and $R^4$ are hydrogen.

In some embodiments, the compound is a compound of Formula Ia:

Ia

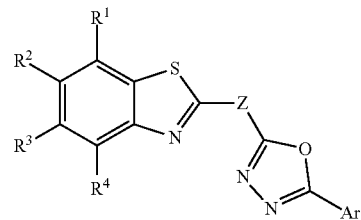

or a pharmaceutically acceptable salt thereof.

In some embodiments, the compound is a compound of Formula Ib:

Ib or a pharmaceutically acceptable salt thereof.

In some embodiments, the compound is a compound of Formula Ic:

Ic or a pharmaceutically acceptable salt thereof; wherein:
$R^{2a}$, $R^{2b}$, $R^{2c}$, $R^{2d}$, and $R^{2e}$ are each independently selected from hydrogen, halo, CN, nitro, hydroxy, $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$ alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino.

In some embodiments of the compounds of Formula Ic, $R^1$, $R^2$, $R^3$, $R^4$, $R^{2a}$, $R^{2b}$, $R^{2c}$, $R^{2d}$, and $R^{2e}$ are each independently selected from hydrogen, halo, CN, hydroxy, $C_{1-6}$ alkyl, $C_{1-6}$ haloalkyl, $C_{1-6}$ alkoxy, and $C_{1-6}$ haloalkoxy.

In some embodiments, X is CH. In some embodiments, X is N.

In some embodiments, the compound is a compound of Formula IIa:

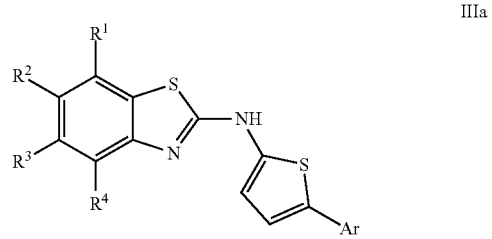

IIa or a pharmaceutically acceptable salt thereof. In some embodiments, the compound is a compound of Formula IIb:

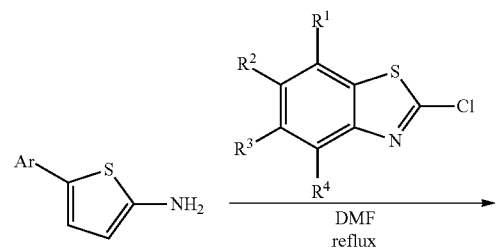

IIb or a pharmaceutically acceptable salt thereof.

In some embodiments, the compound is a compound of Formula IIc:

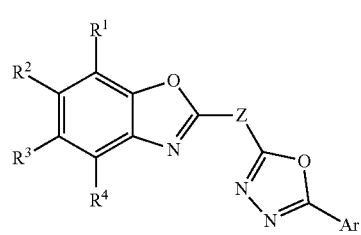

IIc or a pharmaceutically acceptable salt thereof.

In some embodiments, the compound is a compound of Formula IIIa:

IIIa or a pharmaceutically acceptable salt thereof.

Some examples of Formula IIIa may be synthesized using the following synthetic sequence:

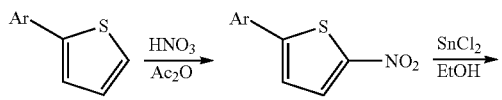

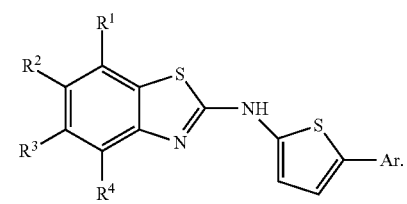

In some embodiments, the compound is a compound of Formula IIIb:

IIIb

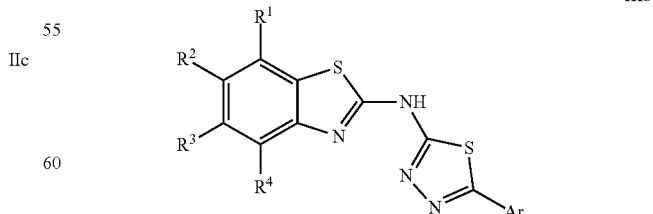

or a pharmaceutically acceptable salt thereof.

Some examples of Formula IIIb may be synthesized using the following synthetic sequence:

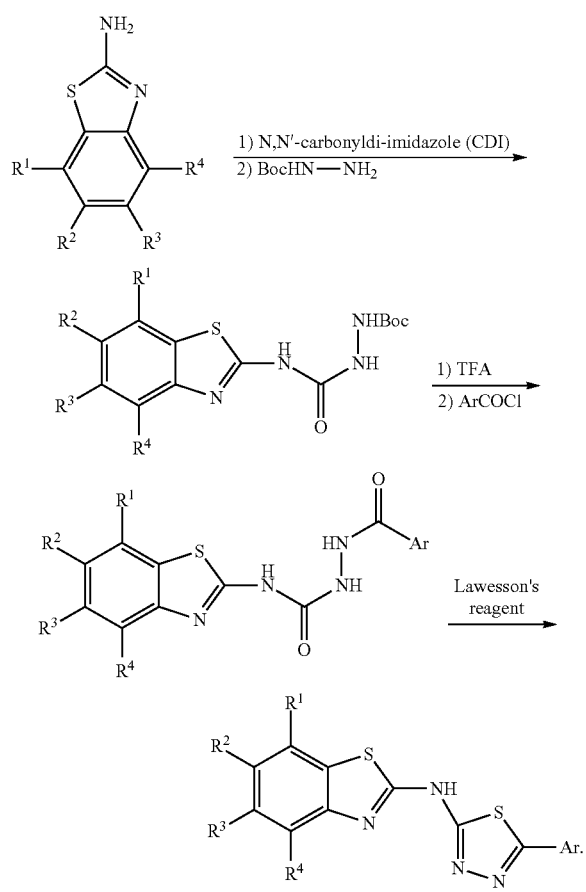

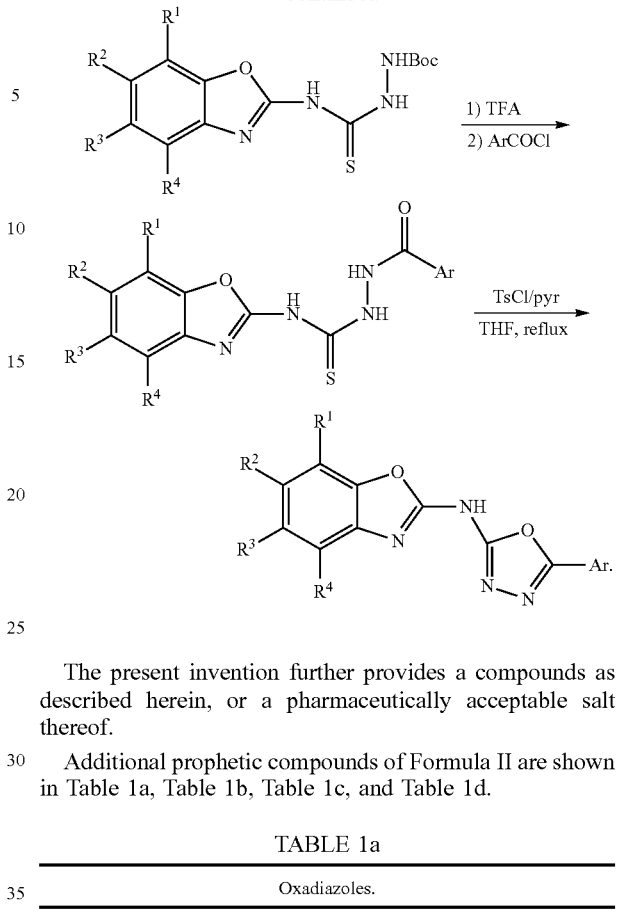

In some embodiments, the compound is a compound of Formula IIIc:

IIIc

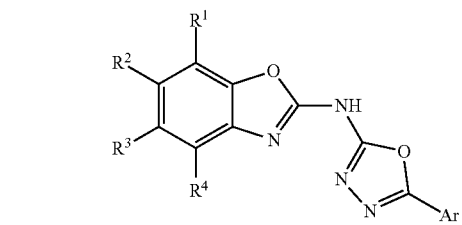

or a pharmaceutically acceptable salt thereof.

Some examples of Formula IIIc may be synthesized using the following synthetic sequence:

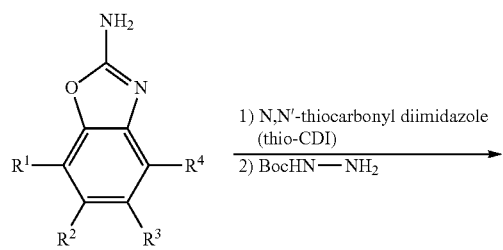

The present invention further provides a compounds as described herein, or a pharmaceutically acceptable salt thereof.

Additional prophetic compounds of Formula II are shown in Table 1a, Table 1b, Table 1c, and Table 1d.

TABLE 1a

Oxadiazoles.

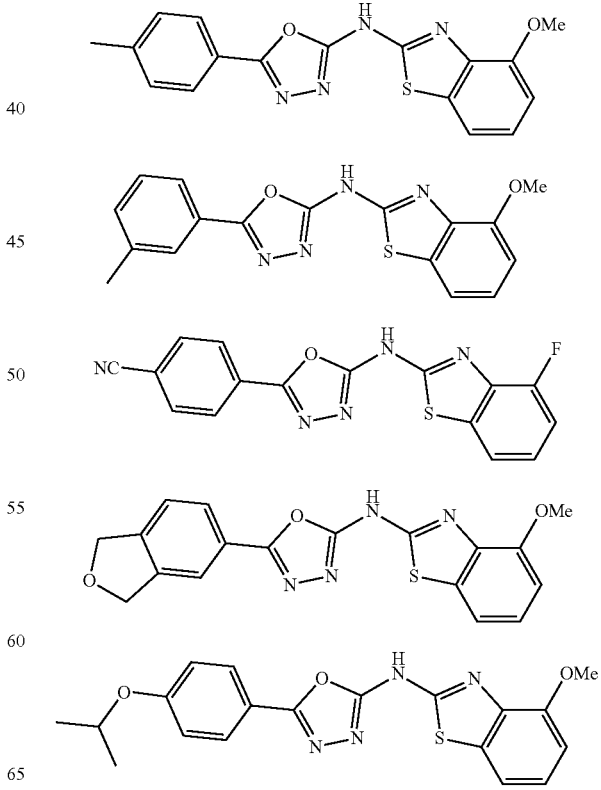

TABLE 1a-continued

Oxadiazoles.

TABLE 1a-continued
Oxadiazoles.
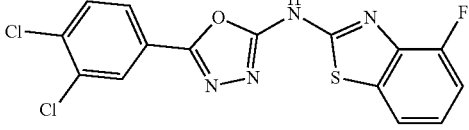
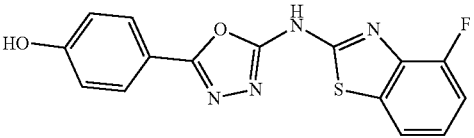 [SMILES: Oc1ccc(-c2nnc(Nc3nc4c(F)cccc4s3)o2)cc1]
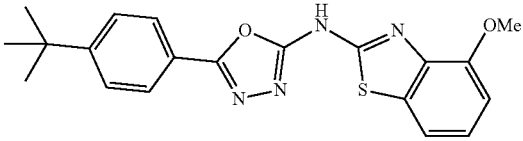 [SMILES: COc1cccc2sc(Nc3nnc(-c4ccc(C(C)(C)C)cc4)o3)nc12]
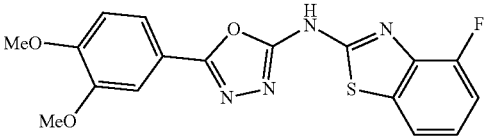 [SMILES: COc1ccc(-c2nnc(Nc3nc4c(F)cccc4s3)o2)cc1OC]
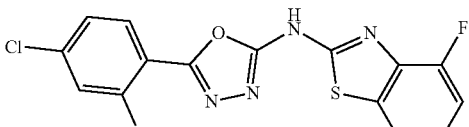
TABLE 1b
Thiadiazoles.
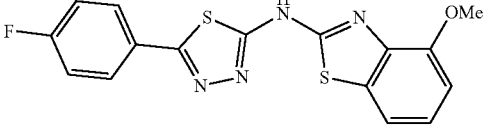
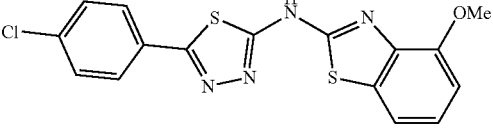
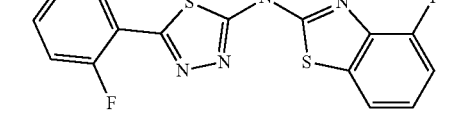
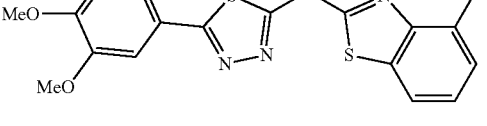
TABLE 1b-continued
Thiadiazoles.
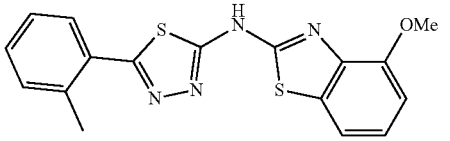 [SMILES: COc1cccc2sc(Nc3nnc(-c4ccccc4C)s3)nc12]
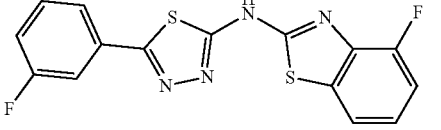
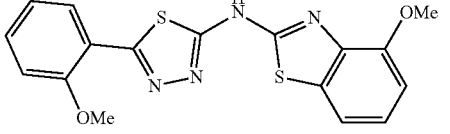
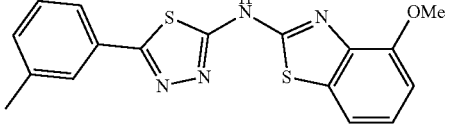
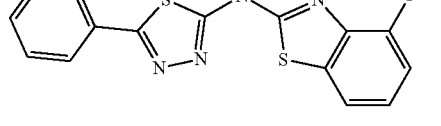
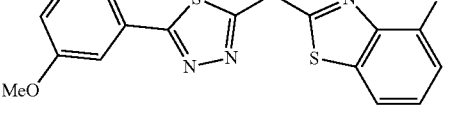
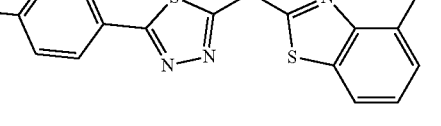
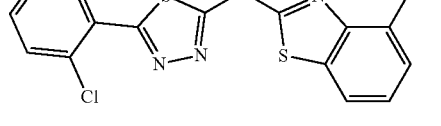
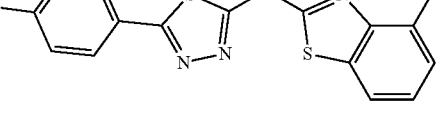
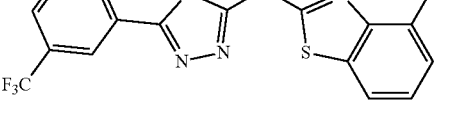

TABLE 1b-continued

Thiadiazoles.

TABLE 1c

Thiophenes.

TABLE 1c-continued

Thiophenes.

TABLE 1c-continued

Thiophenes.

TABLE 1d

Benzoxazoles.

TABLE 1d-continued

Benzoxazoles.

In some embodiments, the compound is a compound of Table 1a, Table 1b, Table 1c, or Table 1d, or a pharmaceutically acceptable salt thereof.

In some embodiments, the compound is selected from:
5-(4-fluorophenyl)-N-(4-methoxybenzo[d]thiazol-2-yl)-1,3,4-oxadiazol-2-amine;
5-(2,4-dimethoxyphenyl)-N-(4-methoxybenzo[d]thiazol-2-yl)-1,3,4-oxadiazol-2-amine;
N-(4-fluorobenzo[d]thiazol-2-yl)-5-phenyl-1,3,4-oxadiazol-2-amine;
N-(6-methoxybenzo[d]thiazol-2-yl)-5-(2-methoxyphenyl)-1,3,4-oxadiazol-2-amine;
N-(6-methoxybenzo[d]thiazol-2-yl)-5-(4-methoxyphenyl)-1,3,4-oxadiazol-2-amine;
5-(4-chlorophenyl)-N-(6-methoxybenzo[d]thiazol-2-yl)-1,3,4-oxadiazol-2-amine;
5-(2-chlorophenyl)-N-(6-fluorobenzo[d]thiazol-2-yl)-1,3,4-oxadiazol-2-amine;
N-(6-fluorobenzo[d]thiazol-2-yl)-5-(4-fluorophenyl)-1,3,4-oxadiazol-2-amine;
N-(6-fluorobenzo[d]thiazol-2-yl)-5-(3-methoxyphenyl)-1,3,4-oxadiazol-2-amine;
N-(6-fluorobenzo[d]thiazol-2-yl)-5-(4-methoxyphenyl)-1,3,4-oxadiazol-2-amine;
N-(5-methoxybenzo[d]thiazol-2-yl)-5-(3-methoxyphenyl)-1,3,4-oxadiazol-2-amine;
N-(5-methoxybenzo[d]thiazol-2-yl)-5-(4-methoxyphenyl)-1,3,4-oxadiazol-2-amine;
N-(5,6-dimethoxybenzo[d]thiazol-2-yl)-5-(4-methoxyphenyl)-1,3,4-oxadiazol-2-amine;
5-(4-methoxyphenyl)-N-(6-(methylthio)benzo[d]thiazol-2-yl)-1,3,4-oxadiazol-2-amine;
N-(4-methoxybenzo[d]thiazol-2-yl)-5-(4-methoxyphenyl)-1,3,4-oxadiazol-2-amine;
N-(4-fluorobenzo[d]thiazol-2-yl)-5-(4-fluorophenyl)-1,3,4-oxadiazol-2-amine;
N-(4-fluorobenzo[d]thiazol-2-yl)-5-(3-methoxyphenyl)-1,3,4-oxadiazol-2-amine; and
N-(4-fluorobenzo[d]thiazol-2-yl)-5-(4-methoxyphenyl)-1,3,4-oxadiazol-2-amine, or a pharmaceutically acceptable salt thereof.

In some embodiments, the compound is selected from:
N-(4-methoxybenzo[d]thiazol-2-yl)-5-(4-methoxyphenyl)-1,3,4-oxadiazol-2-amine;
N-(4-fluorobenzo[d]thiazol-2-yl)-5-(4-fluorophenyl)-1,3,4-oxadiazol-2-amine;
N-(4-fluorobenzo[d]thiazol-2-yl)-5-(3-methoxyphenyl)-1,3,4-oxadiazol-2-amine; and
N-(4-fluorobenzo[d]thiazol-2-yl)-5-(4-methoxyphenyl)-1,3,4-oxadiazol-2-amine, or a pharmaceutically acceptable salt thereof.

In some embodiments, the compound is N-(4-methoxybenzo[d]thiazol-2-yl)-5-(4-methoxyphenyl)-1,3,4-oxadiazol-2-amine, or pharmaceutically acceptable salt thereof.

The compounds described herein can activate SUMO1. Accordingly, the present application further provides a method of activating SUMO1, comprising contacting comprising contacting a cell with a compound, salt, or composition described herein, in an amount effective to activate SUMO1. The contacting can be done in vivo or in vitro. In further embodiments, the compounds of the present application can be used to activate SUMO1 in an individual in need of the activation by administering a compound, salt, or composition described herein, in an amount effective to activate SUMO1.

The present application further provides a pharmaceutical composition comprising any of the compounds described herein, or a pharmaceutically acceptable salt thereof, and at least one pharmaceutically acceptable carrier.

The present application further provides any of the compounds described herein, or a pharmaceutically acceptable salt thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like.

As used herein, "$C_{n-m}$ alkenyl" refers to an alkyl group having one or more double carbon-carbon bonds and having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "di-$C_{n-m}$-alkylamino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6 or 1 to 4 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6 or 1 to 4 carbon atoms.

As used herein, the term "$C_{n-m}$ alkylcarbonyloxy" refers to a group of formula —OC(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6 or 1 to 4 carbon atoms.

As used herein, the term "carbamyl" refers to a group of formula —C(O)—$NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6 or 1 to 4 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{1-4}$ alkylsulfonylamino" refers to a group of formula —NHS(O)$_2$-alkyl, wherein said alkyl has 1 to 4 carbon atoms.

As used herein, the term "aminosulfonyl" refers to a group of formula —S(O)$_2$NH$_2$.

As used herein, the term "$C_{1-4}$ alkylaminosulfonyl" refers to a group of formula —S(O)$_2$NH(alkyl), wherein said alkyl has 1 to 4 carbon atoms.

As used herein, the term "di-$C_{1-4}$ alkylaminosulfonyl" refers to a group of formula —S(O)$_2$N(alkyl)$_2$, wherein each alkyl independently has 1 to 4 carbon atoms.

As used herein, the term "aminosulfonylamino" refers to a group of formula —NHS(O)$_2$NH$_2$, wherein said alkyl has 1 to 4 carbon atoms.

As used herein, the term "$C_{1-4}$ alkylaminosulfonylamino," refers to a group of formula —NHS(O)$_2$NH(alkyl), wherein said alkyl has 1 to 4 carbon atoms.

As used herein, the term "di-$C_{1-4}$ alkylaminosulfonylamino" refers to a group of formula —NHS(O)$_2$N(alkyl)$_2$, wherein each alkyl independently has 1 to 4 carbon atoms.

As used herein, "halo" or "halogen", employed alone or in combination with other terms, includes fluoro, chloro, bromo, and iodo.

As used herein, the term "$C_{n-m}$ haloalkyl", employed alone or in combination with other terms, refers to an $C_{n-m}$ alkyl group having up to {2(n to m)+1} halogen atoms which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6 or 1 to 4 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, or 7 ring-forming carbons ($C_3$-7). Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring.

A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

A "bicyclic $C_{9-10}$ heteroaryl" is bicyclic fused heteroaryl having 9 to 10 ring members.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen or sulfur and having one or more oxidized ring members.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the present application also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present application can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds of the present application, or salts thereof, are substantially isolated. By "substantially isolated" is meant that the compound is at least partially or substantially separated from the environment in which it was formed or detected. Partial separation can include, for example, a composition enriched in the compounds of the present application. Substantial separation can include compositions containing at least about 50%, at least about 60%, at least about 70%, at least about 80%, at least about 90%, at least about 95%, at least about 97%, or at least about 99% by weight of the compounds of the present application, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Combination Therapy

In some embodiments, a compound of the present application, or a pharmaceutically acceptable salt thereof, can be used in combination with another therapeutic agent to treat diseases such as cancer and/or neurological disorders. For example, the additional agent can be a therapeutic agent that is art-recognized as being useful to treat the disease or condition being treated by the compound of the present application. The additional agent also can be an agent that imparts a beneficial attribute to the therapeutic composition (e.g., an agent that affects the viscosity of the composition).

The combination therapy contemplated by the invention includes, for example, administration of a compound of the present application, or a pharmaceutically acceptable salt thereof, and additional agent(s) in a single pharmaceutical formulation as well as administration of a compound of the present application, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

The additional therapeutic agent can be any therapeutic agent useful for the treatment of the disease states of the methods described herein. The additional therapeutic agent can be administered simultaneously or sequentially. In another embodiment, the method further comprises administering to the patient a viral expression vector comprising SERCA2a. In some embodiments, the method further comprises administering to the patient an adeno-associated vector (AAV) comprising SERCA2a. For example, vectors useful in the present methods include, but are not limited to those described in US 2011/0256101, which is incorporated herein by reference in its entirety.

In one embodiment, SERCA2 is incorporated into a viral vector to mediate transfer to a cell. Alternatively, a retrovirus, bovine papilloma virus, an adenovirus vector, a lentiviral vector, a vaccinia virus, a polyoma virus, or an infective virus may be used. Similarly, nonviral methods which include, but are not limited to, direct delivery of DNA such as by perfusion, naked DNA transfection, liposome mediated transfection, encapsulation, and receptor-mediated endocytosis may be employed. These techniques are well known to those of skill in the art, and the particulars thereof do not lie at the crux of the present invention and thus need not be exhaustively detailed herein. For example, a viral vector is used for the transduction of pulmonary cells to deliver a therapeutically significant polynucleotide to a cell. The virus may gain access to the interior of the cell by a specific means such as receptor-mediated endocytosis, or by non-specific means such as pinocytosis The practice of the present application may employ conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

Pharmaceutical Formulations and Dosage Forms

When employed as pharmaceuticals, the compounds of the present application can be administered in the form of pharmaceutical compositions. These compositions can be prepared in a manner well known in the pharmaceutical art, and can be administered by a variety of routes, depending upon whether local or systemic treatment is desired and upon the area to be treated. Administration routes include, but are not limited, to pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This application also includes pharmaceutical compositions which contain, as the active ingredient, the compound of the present application or a pharmaceutically acceptable salt thereof, in combination with one or more pharmaceutically acceptable carriers (excipients). In some embodiments, the composition is suitable for topical administration. In making the compositions of the present application, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the present application may be milled using known milling procedures such as wet milling to obtain a particle size appropriate for tablet formation and for other formulation types. Finely divided (nanoparticulate) preparations of the compounds of the present application can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the present application can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the present application contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the present application contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the present application contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the present application.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present application. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present application.

The tablets or pills of the present application can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present application can vary according to, for example, the particular use for which the treatment is made, the manner of administration of the compound, the health and condition of the patient, and the judgment of the prescribing physician. The proportion or concentration of a compound of the present application in a pharmaceutical composition can vary depending upon a number of factors including dosage, chemical characteristics (e.g., hydrophobicity), and the route of administration. For example, the compounds of the present application can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Synthesis

Compounds of the present application, including salts thereof, can be prepared using known organic synthesis techniques and can be synthesized according to any of numerous possible synthetic routes, for example, by methods analogous to those described in the Examples section.

The reactions for preparing compounds of the present application can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the present application can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC).

Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present application. Cis and trans geometric isomers of the compounds of the present application are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Kits

The present application also includes pharmaceutical kits useful, for example, in the treatment or prevention of any of the disease states described herein, which include one or more containers containing a pharmaceutical composition comprising a therapeutically effective amount of a compound of the present application. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The methods and compounds will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. N-(4-methoxybenzo[d]thiazol-2-yl)-5-(4-methoxyphenyl)-1,3,4-oxadiazol-2-amine

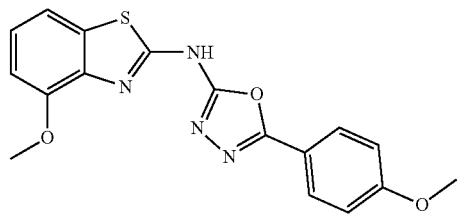 [SMILES: COc1ccc(-c2nnc(Nc3nc4c(OC)cccc4s3)o2)cc1]

4-Methoxybenzhydrazide (0.332 mg, 2.0 mmol) was dissolved in acetonitrile (10 mL) and to this mixture was added 1,1'-thiocarbonyldiimidazole (445 mg, 2.5 mmol). After stirring at rt for 3 hours, 2-amino-4-methoxy-benzothiazole (450 mg, 2.5 mmol) was added and the temperature raised to 85° C. with stirring continued for 20 hours. After cooling, the acetonitrile was removed by rotary evaporator. Water was added (100 mL) and this mixture was extracted with 3 volumes of ethyl acetate (50 mL). The organic layers were collected and solvent removed en vacuo. To this thiosemicarbazide intermediate was added tosyl chloride (393 mg, 2.1 mmol) and pyridine (0.29 mL, 3.6 mmol) in THF (20 mL). The solution was heated to 70° C., bringing the mixture to reflux for 20 h, then cooled. Ethyl acetate (10 mL) and HCl (1.0 M, 10 mL) were added and the mixture was vigorously stirred for 10 minutes. The aqueous layer was removed and extracted with EtOAc (20 mL), and the combined organic layers were flushed with concentrated to a slurry. After purification via reverse-phase HPLC (water/acetonitrile, 10-95%), the product fractions were collected, concentrated and lyophilized to furnish a white solid. ESI-MS m/z 355 [M+H]$^+$.

The following Examples 2-18 were purchased from Life Chemicals Inc., Ontario, Canada.

Example 2. N-(4-fluorobenzo[d]thiazol-2-yl)-5-(4-fluorophenyl)-1,3,4-oxadiazol-2-amine

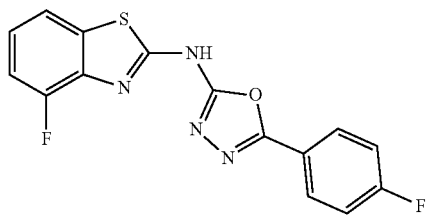 [SMILES: Fc1ccc(-c2nnc(Nc3nc4c(F)cccc4s3)o2)cc1]

Example 3. N-(4-fluorobenzo[d]thiazol-2-yl)-5-(3-methoxyphenyl)-1,3,4-oxadiazol-2-amine

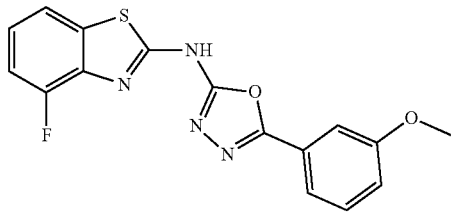 [SMILES: COc1cccc(-c2nnc(Nc3nc4c(F)cccc4s3)o2)c1]

Example 4. N-(4-fluorobenzo[d]thiazol-2-yl)-5-(4-methoxyphenyl)-1,3,4-oxadiazol-2-amine

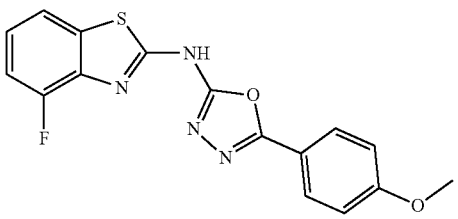 [SMILES: COc1ccc(-c2nnc(Nc3nc4c(F)cccc4s3)o2)cc1]

Example 5. 5-(4-fluorophenyl)-N-(4-methoxybenzo[d]thiazol-2-yl)-1,3,4-oxadiazol-2-amine

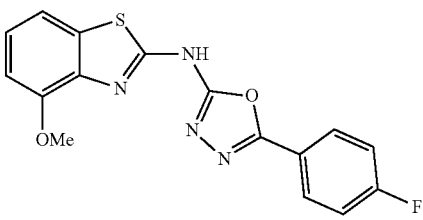 [SMILES: COc1cccc2sc(Nc3nnc(-c4ccc(F)cc4)o3)nc12]

Example 6. 5-(2,4-dimethoxyphenyl)-N-(4-methoxybenzo[d]thiazol-2-yl)-1,3,4-oxadiazol-2-amine

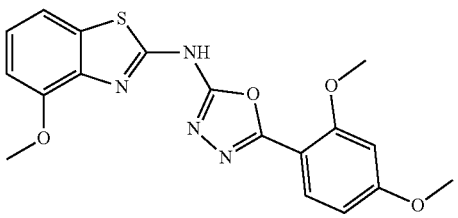 [SMILES: COc1ccc(-c2nnc(Nc3nc4c(OC)cccc4s3)o2)c(OC)c1]

Example 7. N-(4-fluorobenzo[d]thiazol-2-yl)-5-phenyl-1,3,4-oxadiazol-2-amine

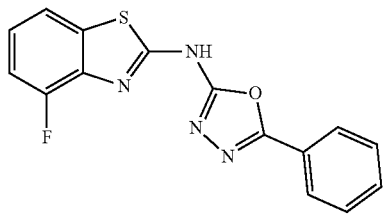 [SMILES: Fc1cccc2sc(Nc3nnc(-c4ccccc4)o3)nc12]

Example 8. N-(6-methoxybenzo[d]thiazol-2-yl)-5-(2-methoxyphenyl)-1,3,4-oxadiazol-2-amine

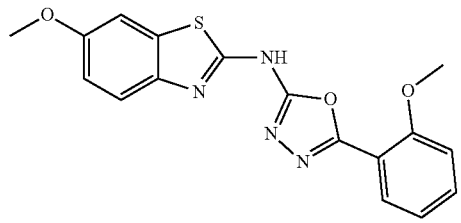 [SMILES: COc1ccc2nc(Nc3nnc(-c4ccccc4OC)o3)sc2c1]

Example 9. N-(6-methoxybenzo[d]thiazol-2-yl)-5-(4-methoxyphenyl)-1,3,4-oxadiazol-2-amine

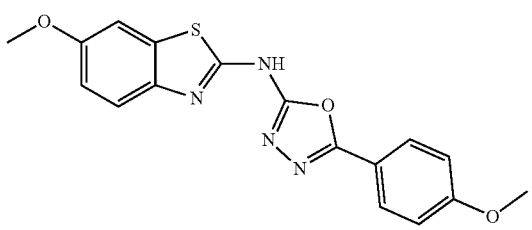

Example 10. 5-(4-chlorophenyl)-N-(6-methoxybenzo[d]thiazol-2-yl)-1,3,4-oxadiazol-2-amine

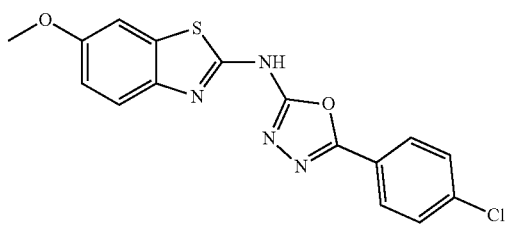 [SMILES: COc1ccc2nc(Nc3nnc(-c4ccc(Cl)cc4)o3)sc2c1]

Example 11. 5-(2-chlorophenyl)-N-(6-fluorobenzo[d]thiazol-2-yl)-1,3,4-oxadiazol-2-amine

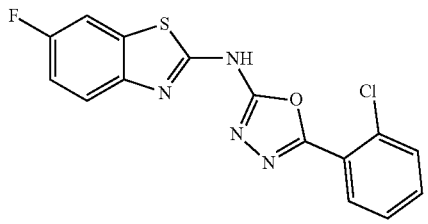 [SMILES: Fc1ccc2nc(Nc3nnc(-c4ccccc4Cl)o3)sc2c1]

Example 12. N-(6-fluorobenzo[d]thiazol-2-yl)-5-(4-fluorophenyl)-1,3,4-oxadiazol-2-amine

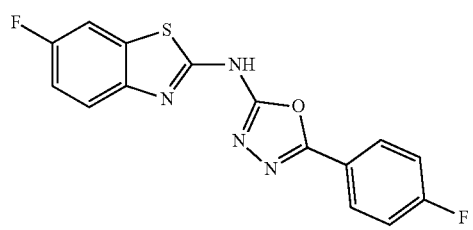 [SMILES: Fc1ccc(-c2nnc(Nc3nc4ccc(F)cc4s3)o2)cc1]

Example 13. N-(6-fluorobenzo[d]thiazol-2-yl)-5-(3-methoxyphenyl)-1,3,4-oxadiazol-2-amine

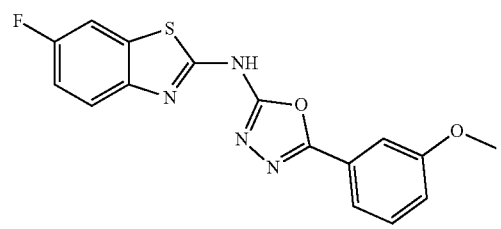 [SMILES: COc1cccc(-c2nnc(Nc3nc4ccc(F)cc4s3)o2)c1]

Example 14. N-(6-fluorobenzo[d]thiazol-2-yl)-5-(4-methoxyphenyl)-1,3,4-oxadiazol-2-amine

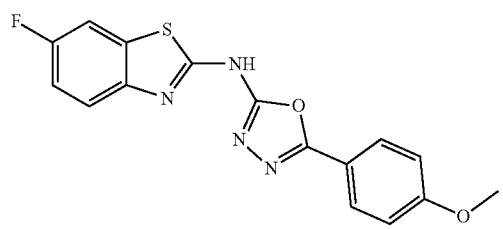 [SMILES: COc1ccc(-c2nnc(Nc3nc4ccc(F)cc4s3)o2)cc1]

Example 15. N-(5-methoxybenzo[d]thiazol-2-yl)-5-(3-methoxyphenyl)-1,3,4-oxadiazol-2-amine

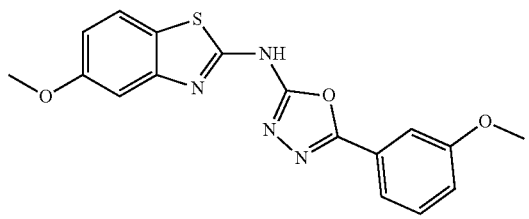

Example 16. N-(5-methoxybenzo[d]thiazol-2-yl)-5-(4-methoxyphenyl)-1,3,4-oxadiazol-2-amine

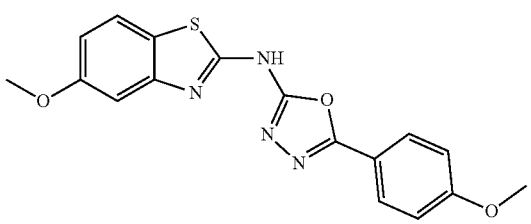

Example 17. N-(5,6-dimethoxybenzo[d]thiazol-2-yl)-5-(4-methoxyphenyl)-1,3,4-oxadiazol-2-amine

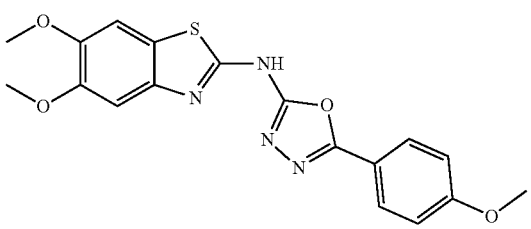

Example 18. 5-(4-methoxyphenyl)-N-(6-(methylthio)benzo[d]thiazol-2-yl)-1,3,4-oxadiazol-2-amine

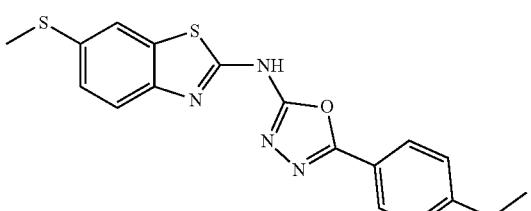

Materials and Methods
Antibodies and Transfection

The following antibodies were used for immunoblotting and immunoprecipitation (IP): polyclonal anti-SERCA2a (21th century Biochem Inc.), monoclonal anti-GAPDH (Sigma-Aldrich, catalog no. G8795), monoclonal anti-SUMO 1 (Cell Signaling Technology Inc., catalog no. 4930), anti-mouse horseradish peroxidase (HRP) (Pierce Biotechnology Inc., catalog no. 32430), and anti-rabbit HRP (Pierce Biotechnology Inc., catalog no. 32460). YFP-tagged SUMO1, pcDNA3.0-SERCA2a, and HA-tagged Ubc9 plasmids were used for the transfection. The plasmid DNA was amplified in the *Escherichia coli* strain DH5a and extracted by using a commercial purification kit (Qiagen, catalog no. 12263). Purified plasmid was resuspended in sterile TE buffer (10 mM Tris-HCl and 1 mM EDTA, pH 7.6). Only the preparation highest purity (A260/A280>1.8) was used for transfection. 1 µg of each plasmid was used for transfection. HEK-293 cells (American Type Culture Collection, catalog no. CRL-1873) were grown at 37° C. and under a 5% CO2 humidified atmosphere in Dulbecco's modified Eagle's medium (DMEM, Cellgro, catalog no. 10-0 13-CM) containing 10% fetal bovine serum (SAFC Bioscience, catalog no. 12107) and 100 i.u of penicillin/ml and 100 µg of streptomycin/ml. HEK-293 cells were seeded at a density of $3-5\times10^5$ cells per 60 mm culture dish in DMEM. The cells were transiently transfected using Lipofectamine 2000 (Invitrogen, catalog no. 11668) with indicated expression plasmids. After 24 hours, the cells were treated with either small molecules or dimethyl sulfoxide (DMSO, Sigma-Aldrich, catalog no. D2650).

Cardiac Myocyte Isolation

Calcium-tolerant adult rat ventricular myocytes (ARVMs) were obtained from hearts of male Sprague-Dawley rats (250 to 300 g). The heart was excised and perfused with a standard enzymatic technique. ARVMs were plated on multi-chambered plates or culture dishes, pre-coated with laminin 2 µg/cm$^2$, at a density of 10$^5$ cells/cm$^2$ in DMEM without L-glutamine supplemented with 10 mmol/l HEPES, 3.7 mg/ml NaHCO$_3$, 1 mg/ml glucose, 0.11 mg/ml sodium pyruvate, 2 mg/ml bovine serum albumin, 2 mmol/1 L-camitine, 5 mmol/1 creatine, 5 mmol/1 taurine, 1% penicillin-streptomycin, and 1% gentamycin. Following isolation, cells were allowed to settle for 1 hour. Cultures were incubated at 37° C., in an atmosphere of 5% CO$_{2-95}$% air. Fresh medium was added gently as medium was being drawn off until the cultures had been thoroughly washed. Only quiescent, rod-shape cardiac myocytes were selected for IonOptix experiments.

Example Compounds

Each compound was added at 10 µM. DMSO was used as a control. After 24 hours at 37° C., SERCA2a SUMOylation and functional analysis were determined.

Cell Image

Cellular permeability and potential activity of the compounds were examined by tracking of the YFP-SUMO1. HEK-293 cells expressing YFP-SUMOl and pcDNA3.0-SERCA2a were incubated with either 10 µM DMSO or 10 µM small molecules for 24 hours at 37° C. Fluorescent signals were monitored by fluorescence microscopy. HA-tagged Ubc9 expressing cells were served as a positive control.

Cell Shortening/Re-Lengthening

Mechanical properties of ARVMs were assessed using an IonOptix MyoCam® system (IonOptix, Milton, Mass.). In brief, cells were placed in a Warner chamber mounted on the stage of an inverted microscope (Olympus, IX-70) and superfused (1 ml/min at 30° C.) with a buffer containing 131 mM NaCl, 4 mM KCl, 1 mM CaCh, 1 mM MgCh, 10 mM glucose, and 10 mM HEPES, pH 7.4. ARVMs were field stimulated with suprathreshold voltage and at a frequency of 0.5 Hz. The ARVMs being studied was displayed on the computer monitor using an IonOptix MyoCam camera. SoftEdge software (IonOptix) was used to capture changes in cell length during shortening and re-lengthening.

Intracellular Fluorescence Measurement

ARVMs were placed in a chamber on an Olympus IX-70 inverted microscope and imaged through a Fluor 40× oil objective. ARVMs were exposed to light emitted by a 75 W lamp and passed through either a 360 or a 380 nm filter (bandwidths were ±15 nm), while being stimulated to contract at 0.5 Hz. Fluorescence emissions were detected between 480 and 520 nm by a photomultiplier tube after first illuminating cells at 360 nm for 0.5 s then at 380 nm for the duration of the recording protocol (333 Hz sampling rate). The 360 nm excitation scan was repeated at the end of the protocol and qualitative changes in intracellular $Ca^{2+}$ concentration ($(Ca^{2+}]_i$) were inferred from the ratio of the fluorescence intensity at two wavelengths.

Immunoblotting

Equal amounts of protein from either small molecule treated or DMSO treated cells or immunoprecipitates were resolved by 7.5% SDS-PAGE and transferred to nitrocellulose membranes (Bio-Rad, catalog no. 162-0112). The membranes were blocked for 1 hour at room temperature with 5% non-fat milk (Cell Signaling Technology Inc., catalog no. 9999) in TBST (10 mM Tris-HCl, 150 mM NaCl, and 0.05% tween-20, pH 8.0). The blots were incubated with specific primary antibodies at 4° C. for overnight. The blots were then washed five times for 10 minutes each with TBST and incubated for 1 hour with HRP-conjugated secondary antibodies in TBST with 5% non-fat milk. After five times TBST washes, the protein bands were visualized with enhanced chemiluminescence (Pierce Biotechnology Inc., catalog no. 32132) and exposed to x-ray film (Denville Scientific Inc., catalog no. E3012). GAPDH expression provided an internal control.

SERCA2a SUMOylation Assay

Post-transfection (48 hours), the HEK-293 cells were rinsed twice with phosphate-buffered saline (PBS, Cellgro, catalog no. 21-040-CM) and lysed in 1% Nonidet P-40 lysis buffer (Boston Bioproducts, catalog no. BP-119) with 10 mM N-ethylmaleimide (NEM, Sigma-Aldrich, catalog no. N3876) and phosphatase inhibitor cocktail (Complete Mini Tablet, Roche Applied Science, catalog no. 11836153001). 2 mg of protein were mixed with the anti-SERCA2a antibodies for overnight at 4° C. in lysis buffer. Pre-washed protein A-Separose beads (Pierce Biotechnology Inc., catalog no. 20333) was added to each sample and incubated 1 hour at 4° C. with gentle rocking. Immunocomplexes were washed with lysis buffer three times and precipitated by centrifugation at 12000×g for 10 seconds. The immunocomplexes were resuspended in SDS sample buffer and subjected to immunoblotting. Controls for the immunoprecipitations were performed using an anti-rabbit IgG equal to that of the primary precipitating antibody. Ten percent of whole cell lysates used in the immunoprecipitation was loaded for subsequent immunoblotting.

Statistics

Data were obtained from experiments performed two or three times and values are presented as mean±standard deviation (SD). The p value was calculated by analysis of variance, followed by Student's t test. Difference between the groups of data were considered statistically significant when p<0.05.

Compound Screening Data

Figure 7A:
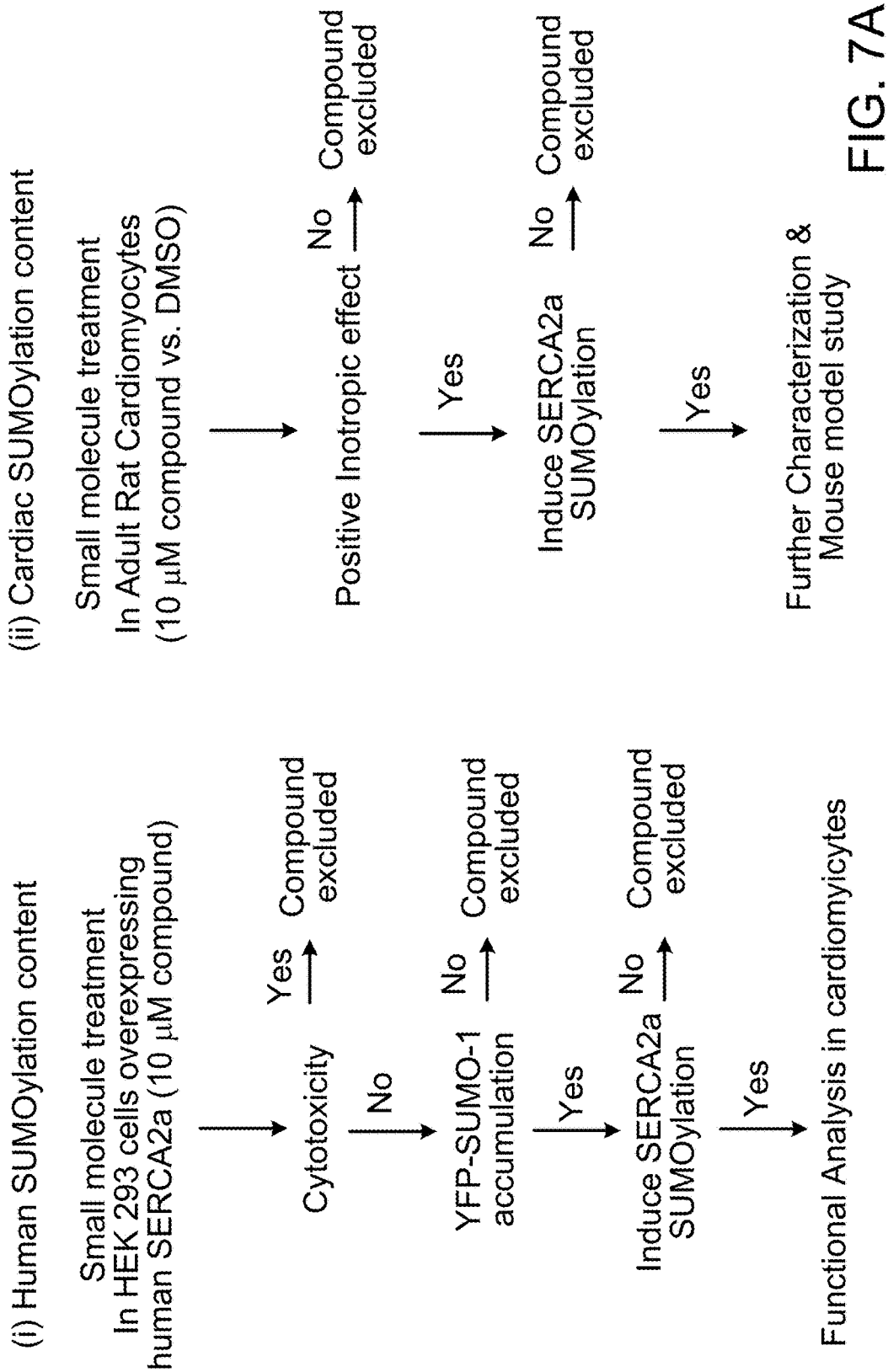
FIG. 7A depicts the compound screening strategy used to identify Example 1 that targets the SERCA2a SUMOylation.
Figure 7B:
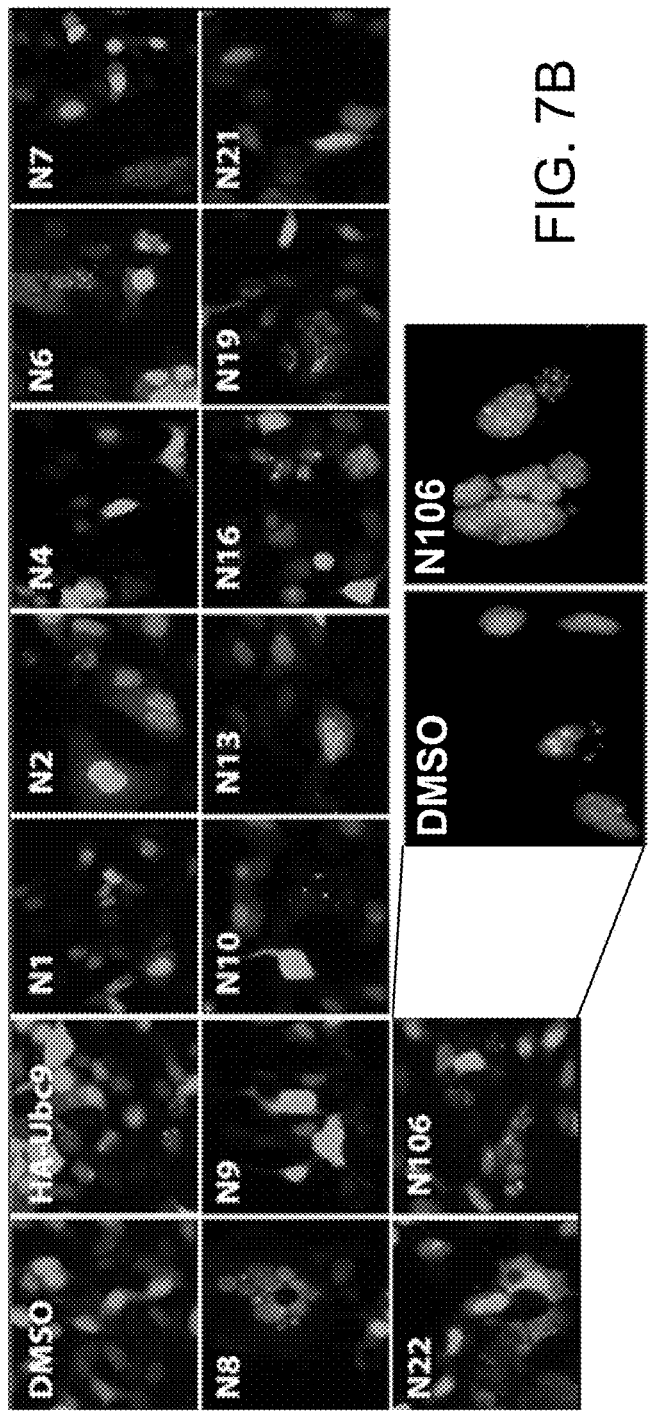
FIG. 7B depicts cellular imaging of HEK-293 cells with Example 1 at 10 µM concentration.
Figure 7C:
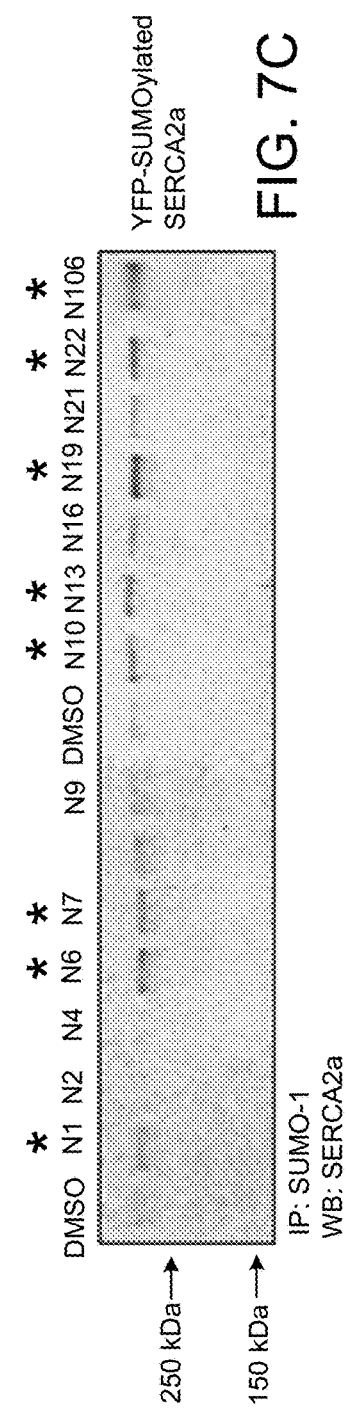
FIG. 7C depicts a blot of the effect of Example 1 on increasing SERCA2a SUMOylation in HEK-293 cells.
Figure 8A:
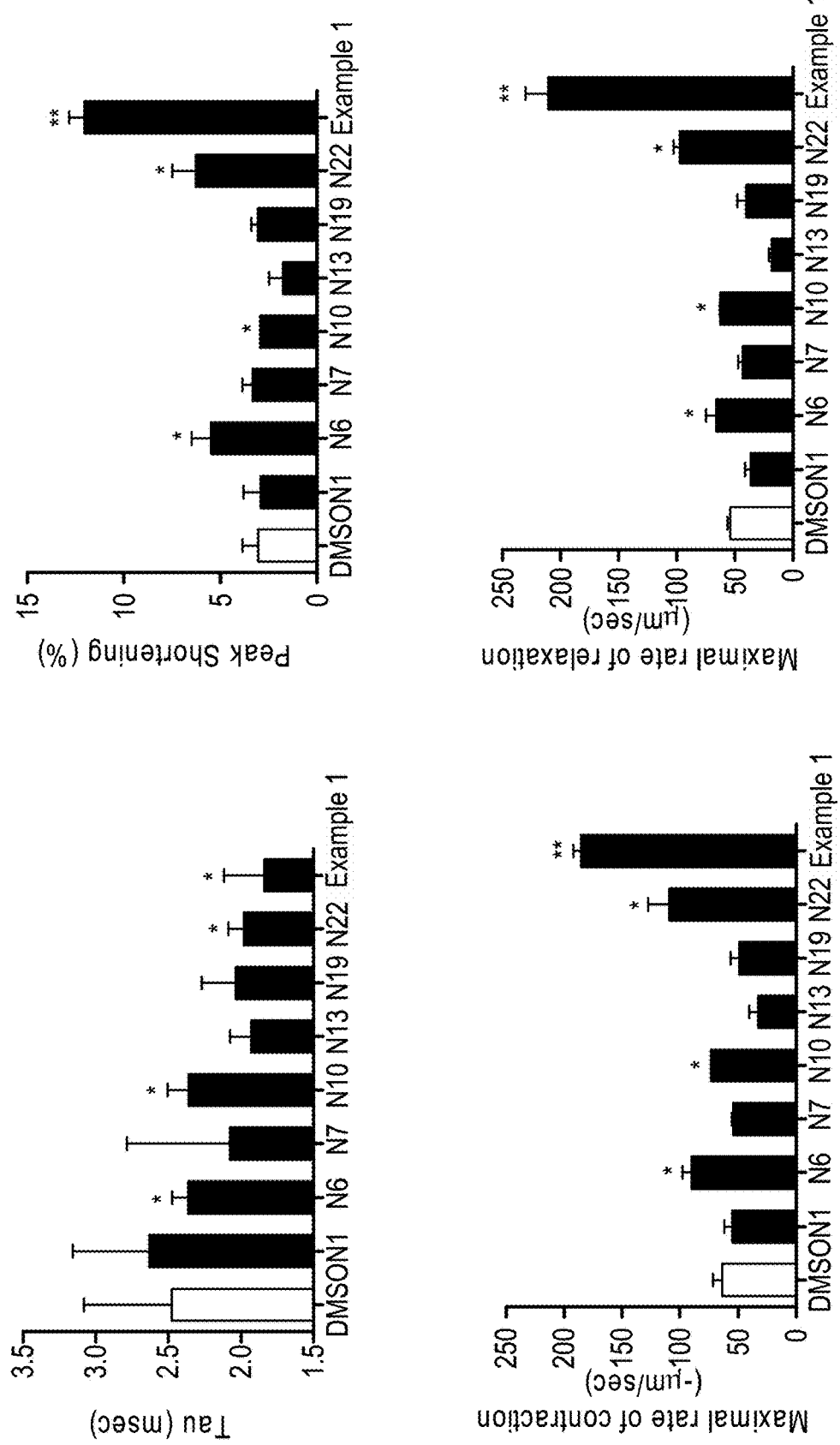
FIG. 8A depicts the functional analysis of Example 1 compared to other compounds identified from the screening strategy.
Figure 8B:
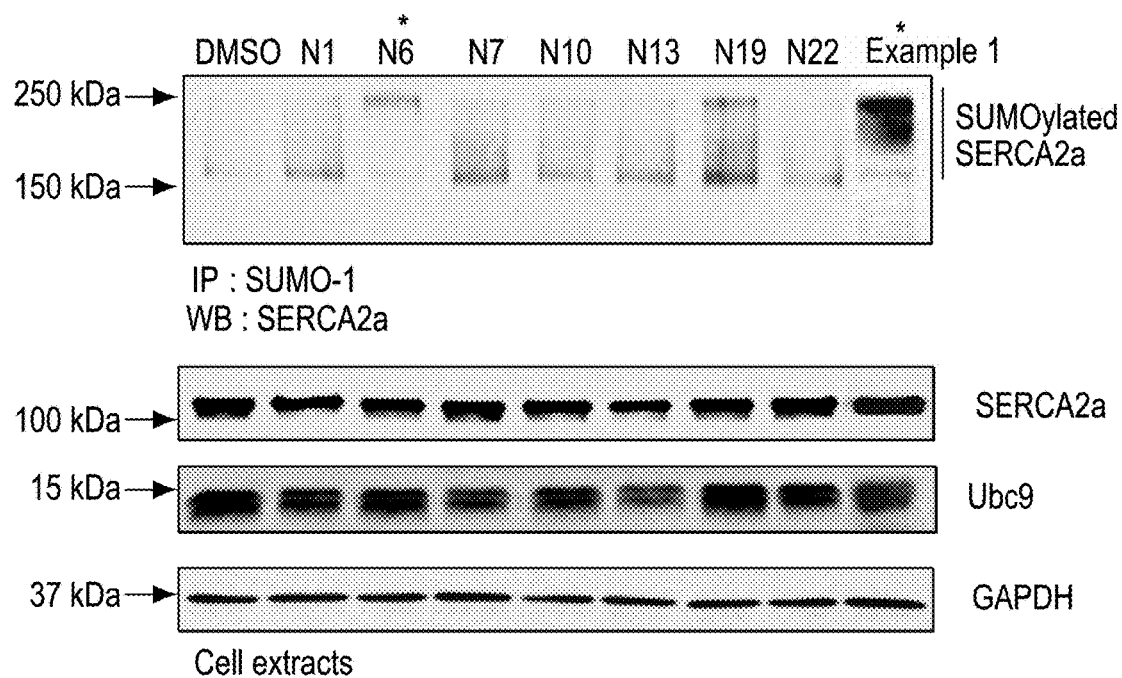
FIG. 8B depicts endogenous SERCA2a SUMOylation status for 8 compounds and a vehicle.

Referring to FIG. 7, thirty small molecules were screened for their ability to SUMOylate SERCA2a in HEK-293 cells at 10 µM concentration. Fourteen non-cytotoxic compounds were used. Referring to FIG. 7b, cellular activity of the compounds was confirmed by using cell-imaging step. Of the fourteen compounds tested, referring to FIG. 7c, eight compounds were selected based on their effect on increasing SERCA2a SUMOylation in HEK-293 cells. The mechanical properties of the eight compounds were assessed by using IonOptix system. Referring to FIG. 8a, four of these compounds were found to increase cell contractility and tau significantly (p<0.05). Referring to FIG. 8b, endogenous SERCA2a SUMOylation status was also determined in the same set of cells. Only two compounds showed both positive inotrophic effect and enhancement of endogenous SERCA2a SUMOylation.

Figure 1B:
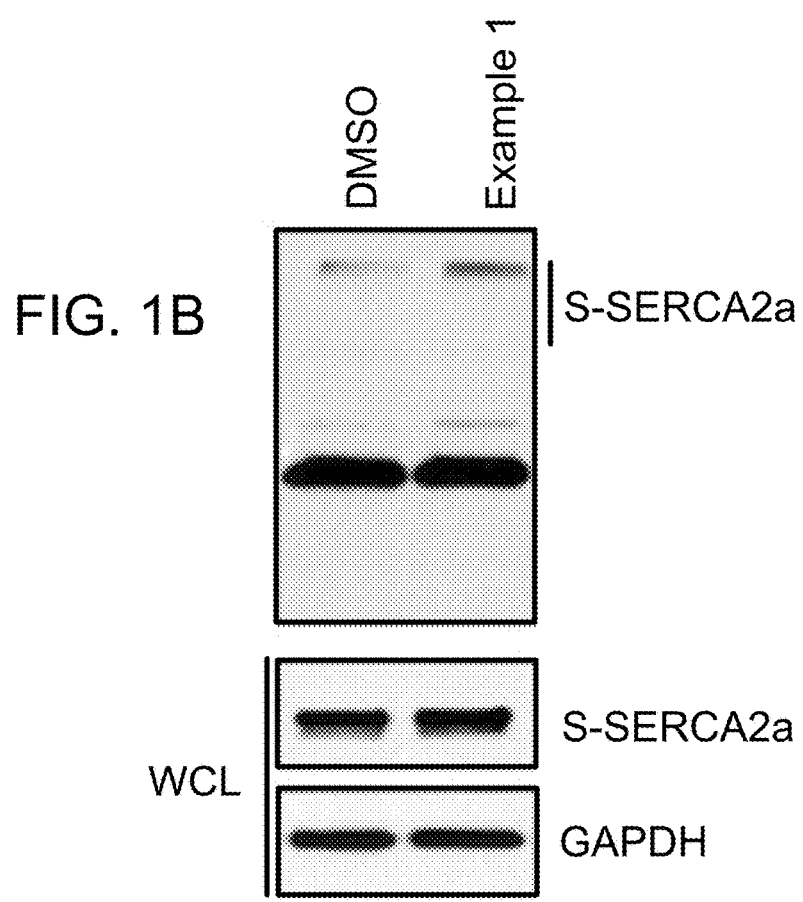
FIG. 1B depicts immunoblotting from cells treated with Example 1 or DMSO.

Example A: Induction of YFP-SUMO1 Accumulation and SERCA2A SUMOylation in HEK-293 Cells The ability of the Example compound to SUMOylate SERCA2a was examined using an in vitro system in HEK 293 cells where both SERCA2a and SUMO 1 are expressed. The cellular permeability and potential activity of the Example compounds was examined by tracking of the YFP-SUM01. HEK-293 cells expressing YFP-SUM01 and pcDNA3.0-SERCA2a were treated with either 10 µM DMSO or 10 µM indicated Example 1 for 24 hrs. Fluorescent signals were monitored by fluorescence microscopy. HA-Ubc9 expressing cells were served as a positive control. The results are shown in FIG. 1A (scale bars, 10 µM). The SERCA2a SUMOylation profiling was then analyzed by using the same cells (FIG. 1B, WCL, whole cell lysates; S-SERCA2a, SUMOylated SERCA2a).

Figure 2A:
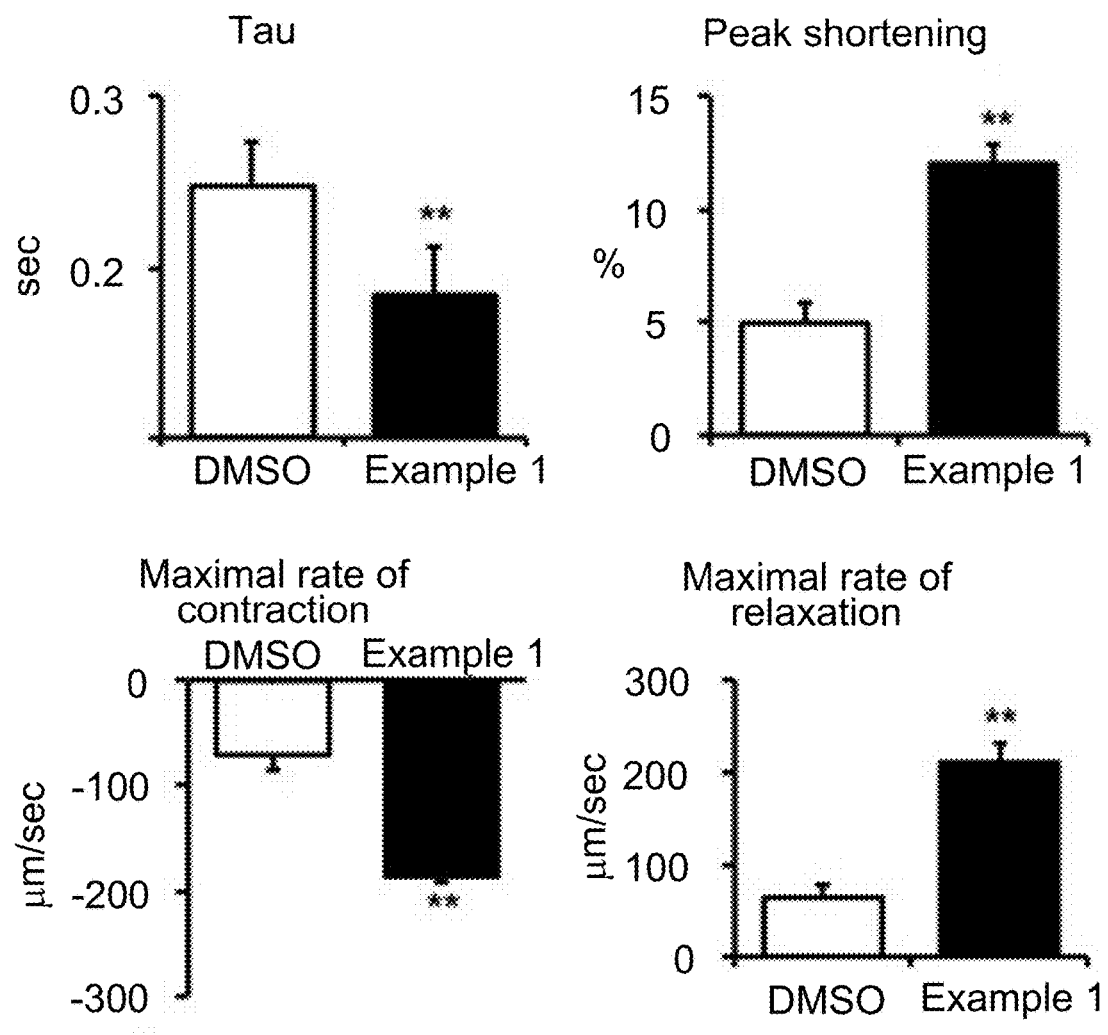
FIG. 2A depicts effects of Example 1 on the mechanical properties of the ARVMs from measurements using a video-based edge detection system (IonOptix).
Figure 2B:
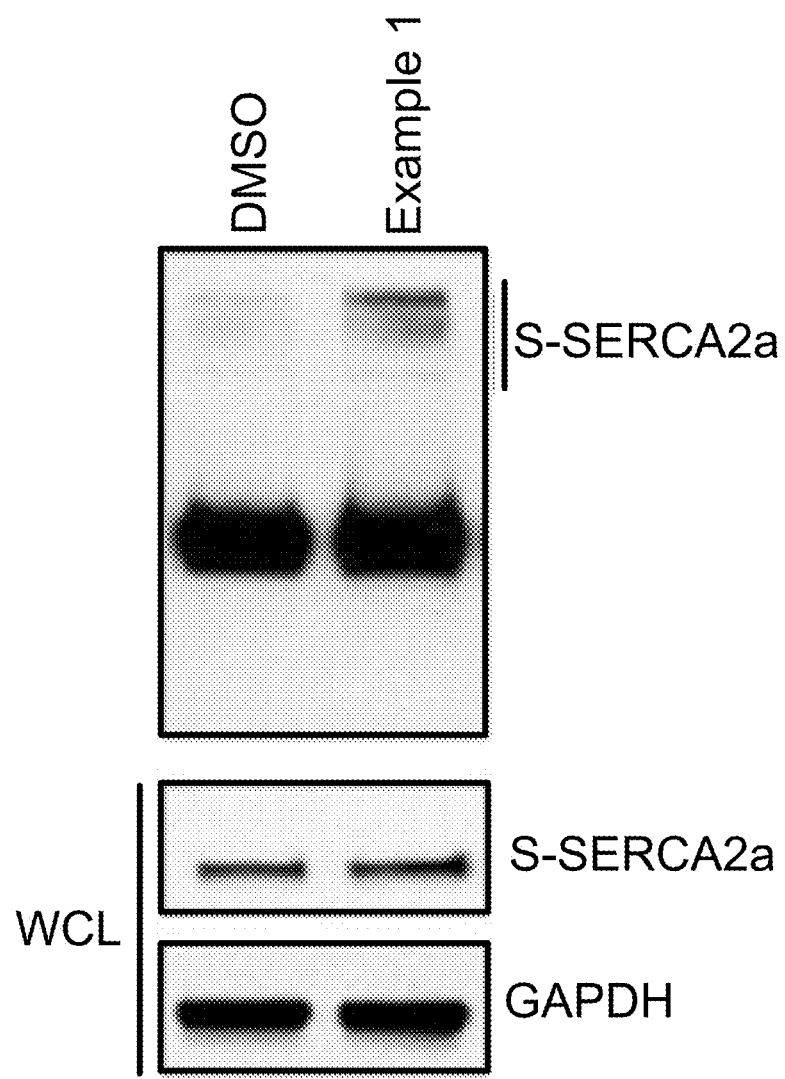
FIG. 2B depicts SERCA2a SUMOylation profiling in the same set of ARVMs.

Example B: Effect of Example 1 on Intracellular Calcium Decay, Cell Contractility and SERCA2a SUMOylation in Isolated Adult Cardiomyocytes The effects of the Example compound was examined on isolated rat cardiomyocytes shortening and relaxation parameters. Example 1 showed positive inotropic and lusitropic effects on cardiac function. Effects of Example 1 on mechanical properties of the ARVMs were assessed using a video-based edge detection system (IonOptix). The time constant of the increase of force during the stretch decreased (tau), percentage of peak shortening (PS), maximal rate of relaxation and contraction were analyzed at 24 hrs postincubation of the compounds in culture media (N=10 ARVMs). The mechanical data were analyzed with student's t-test (FIG. 2A, P<0.05 compared to the DMSO treated cells). SERCA2a SUMOylation profiling was analyzed in a same set of ARVMs (FIG. 2B, WCL, whole cell lysates; S-SERCA2a, SUMOylated SERCA2a).

Example C: Effect of Example 1 on SERC2a Function

Figure 3A:
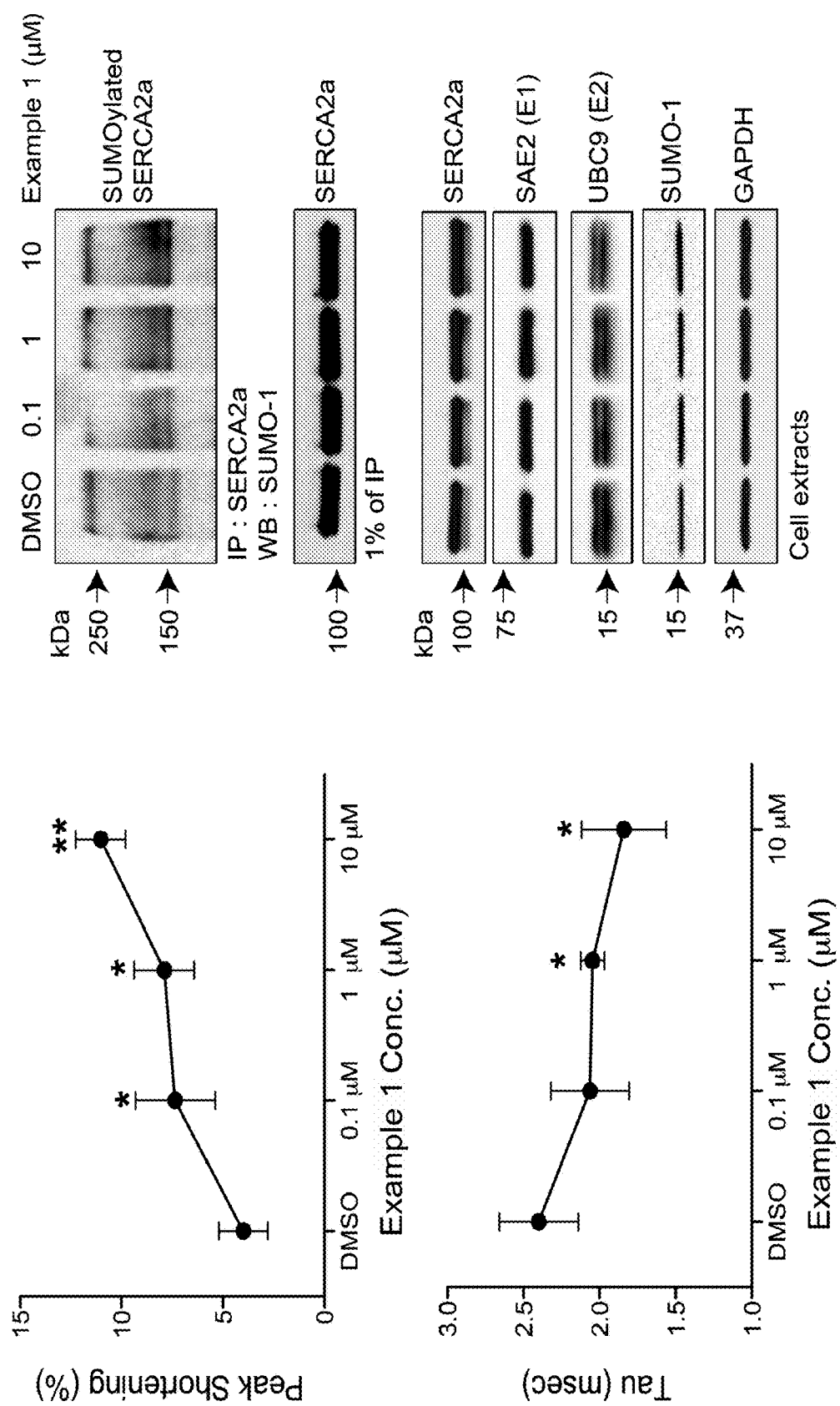
FIG. 3A depicts dose-dependent effects of Example 1 of a SERCA2a SUMOylation activator.
Figure 3B:
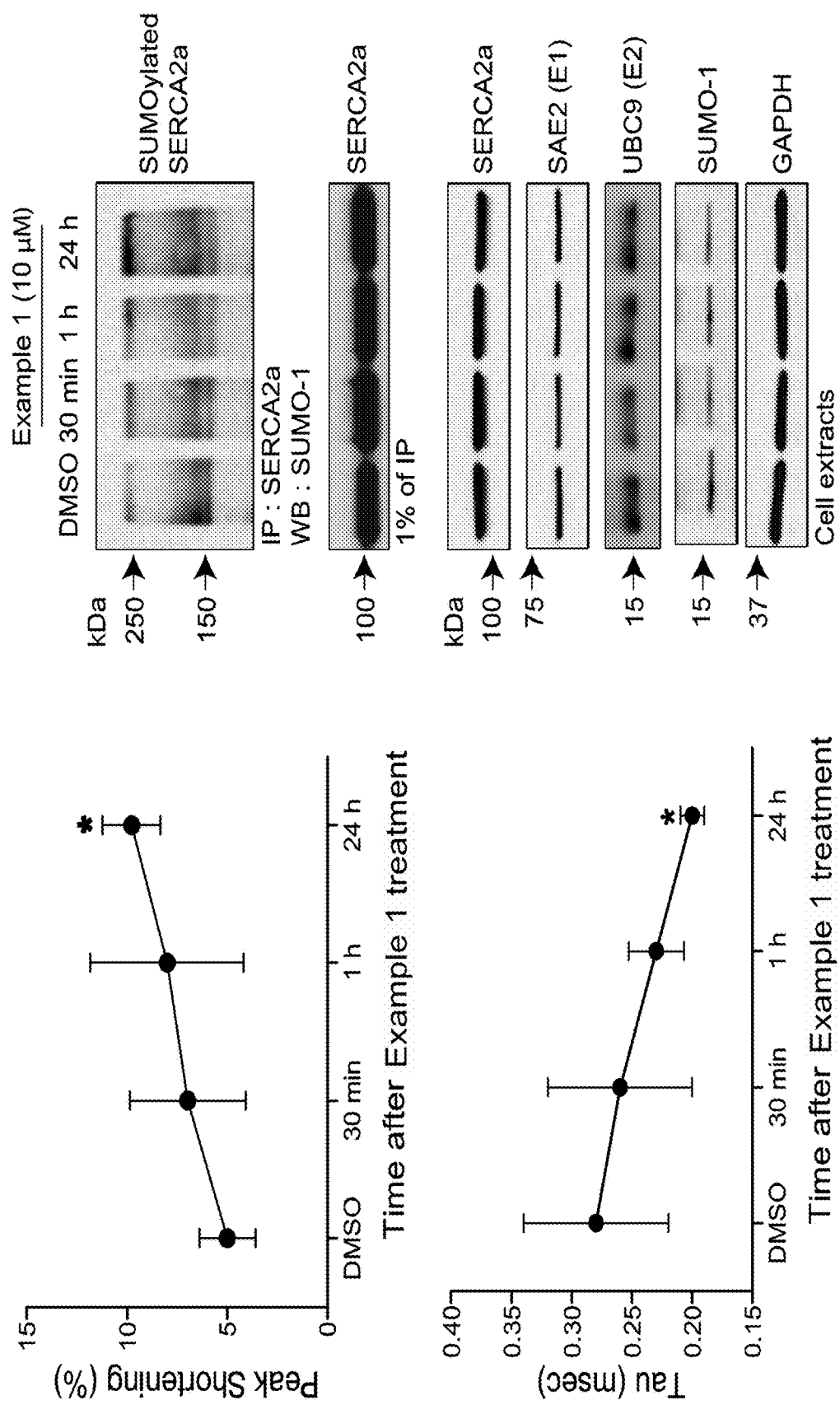
FIG. 3B depicts time-dependent effects of Example 1 of a SERCA2a SUMOylation activator.

Treatment with Example 1 significantly increased the rate of transient calcium decay (Tau (msec); Example 1, 1.8±0.2; DMSO, 2.4±0.2, p<0.05), and cell contraction (Peak shortening (%); Example 1, 12.0±0.8, DMSO, 3.0±0.8; Maximal rate of contraction (µm/sec); Example 1, −185.5±6.5, DMSO, −64.0±7.9; Maximal rate of relaxation (µm/sec); Example 1, 210.7±19.4, DMSO, 54.0±2.4, p<0.001, n=10) and endogenous SERCA2a SUMOylation in isolated rodent adult cardiomyocytes (FIG. 8a). To further validation the efficiency of Example 1 for cardiac function, we performed dose response experiments. The results indicated that Example 1 significantly increased cell contractility (peak shortening (%); p<0.05, versus DMSO and 10 μM; p<0.001, versus DMSO) in a concentration dependent manner. Tau value, which is an indicator of SERCA2a pump function, was also significantly decreased with an increasing amount of Example 1 (0.1 μM Example 1, 1.3±0.0 msec, 1 μM Example 1; 1.3±0.1 sec, p<0.05, versus DMSO and 10 μM Example 1, 1.0±0.1 msec, p<0.001, versus DMSO) (FIG. 3b, left). In addition, increasing Example 1 increased levels of SERCA2a SUMOylation (FIG. 3b, right). However, the protein expression levels of E1, E2 enzymes, SERCA2a and SUMO-1 were not changed.

Example D: Effect of Example 1 on the SUMO Activating Enzyme, E1

Figures 4C, 4D:
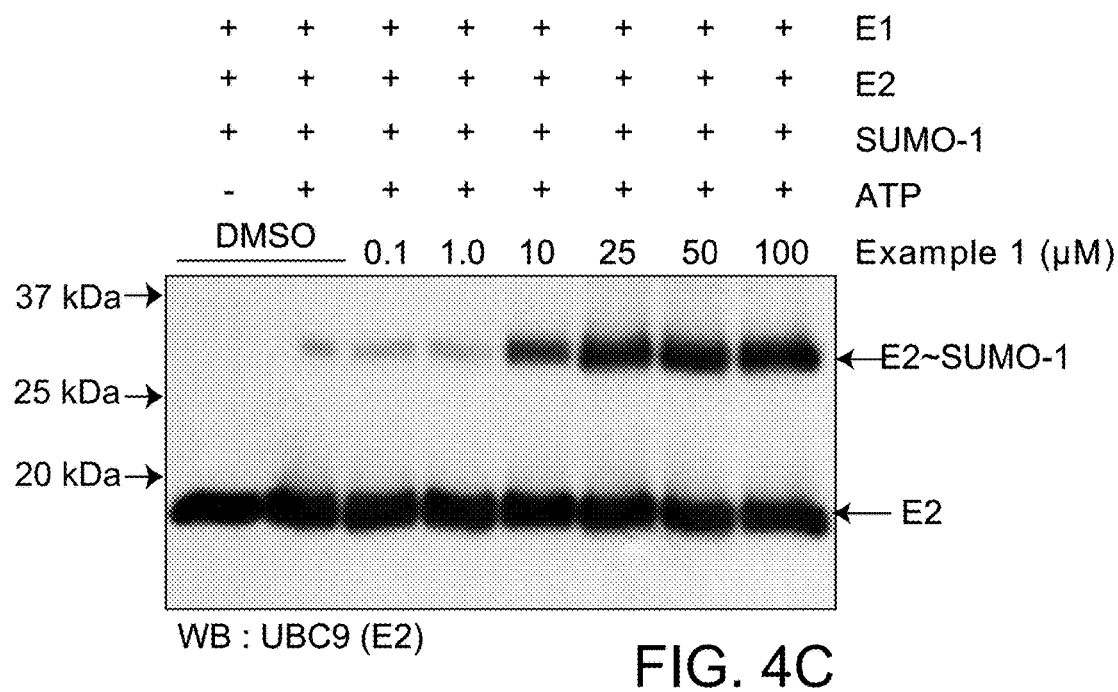
FIG. 4C depicts a blot of transfer of the activated SUMO-1 from SUMO E1 to the unique SUMO E2 enzyme.
FIG. 4D depicts computer modeling of the $EC_{50}$ of PPi, E1-SUMO-1, and E2-SUMO1.
Figure 5A:
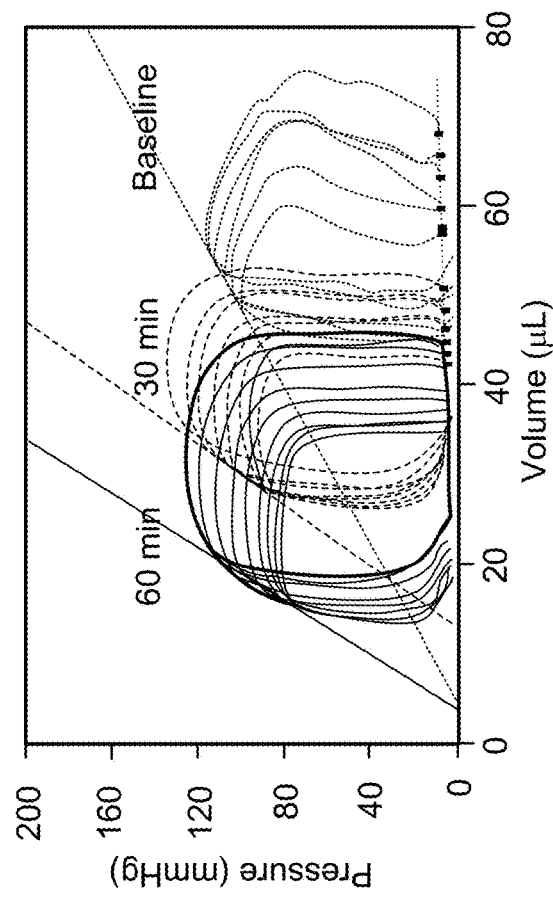
FIG. 5A depicts time-dependent effects of Example 1 in mouse models.
Figure 5A:
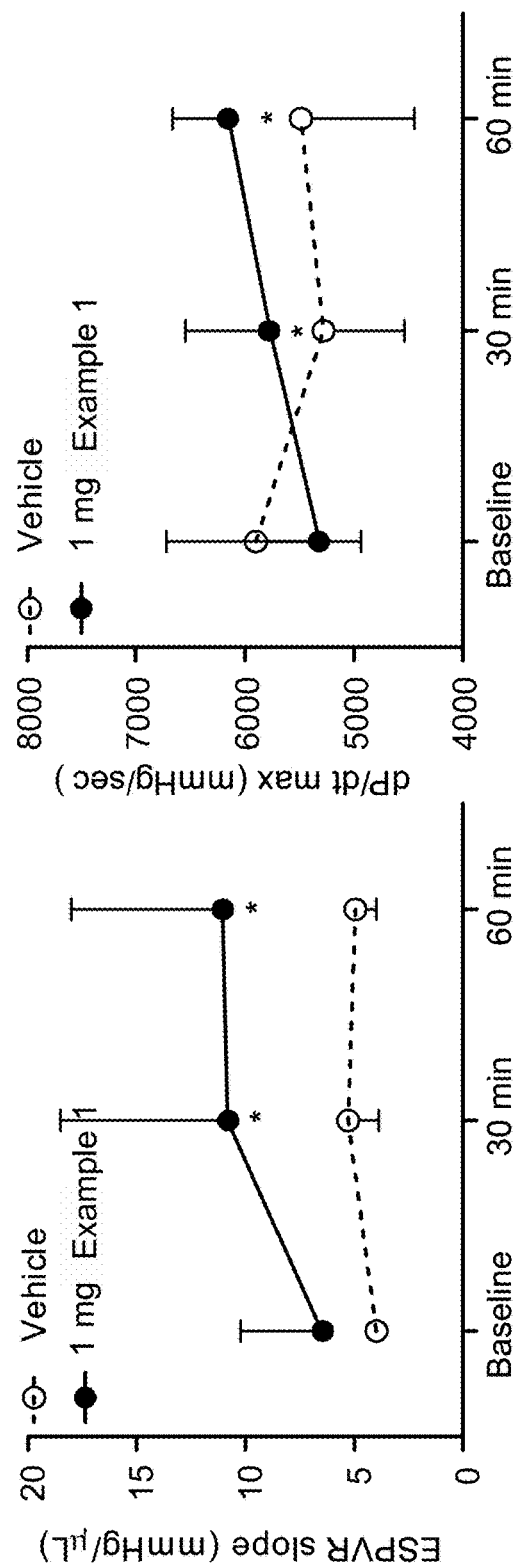
Figure 5B:
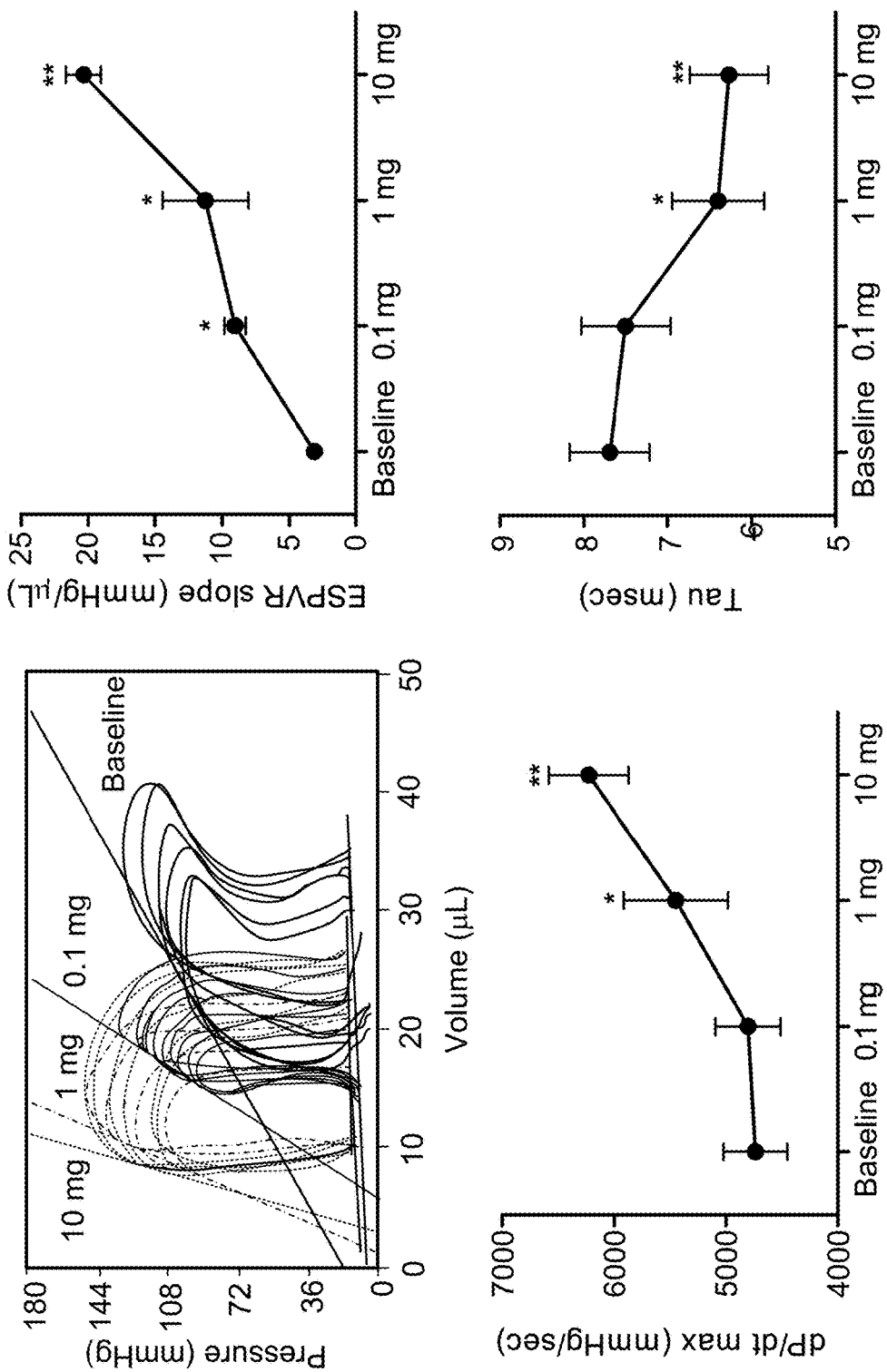
FIG. 5B depicts dose-dependent effects of Example 1 in mouse models.

Example 1 activated ATP-dependent activation of SUMO-1 ($EC_{50}$=40.47±4.4 μM, FIG. 4a) and thioester formation between the SUMO-1 and SUMO E1 enzyme ($EC_{50}$=1.85±0.96 μM, FIG. 4b) and subsequent transfer of the activated SUMO-1 from SUMO E1 to the unique SUMO E2 enzyme, UBC9 ($EC_{50}$=10.17±0.28 μM, FIG. 4c) in a gel-based assay. To better understand the structural basis for the action of Example 1 on SUMO E1 enzyme, in silico modeling was also performed (FIG. 4d).

Example E: Effect of Example 1 on Contractility

Figure 9A:
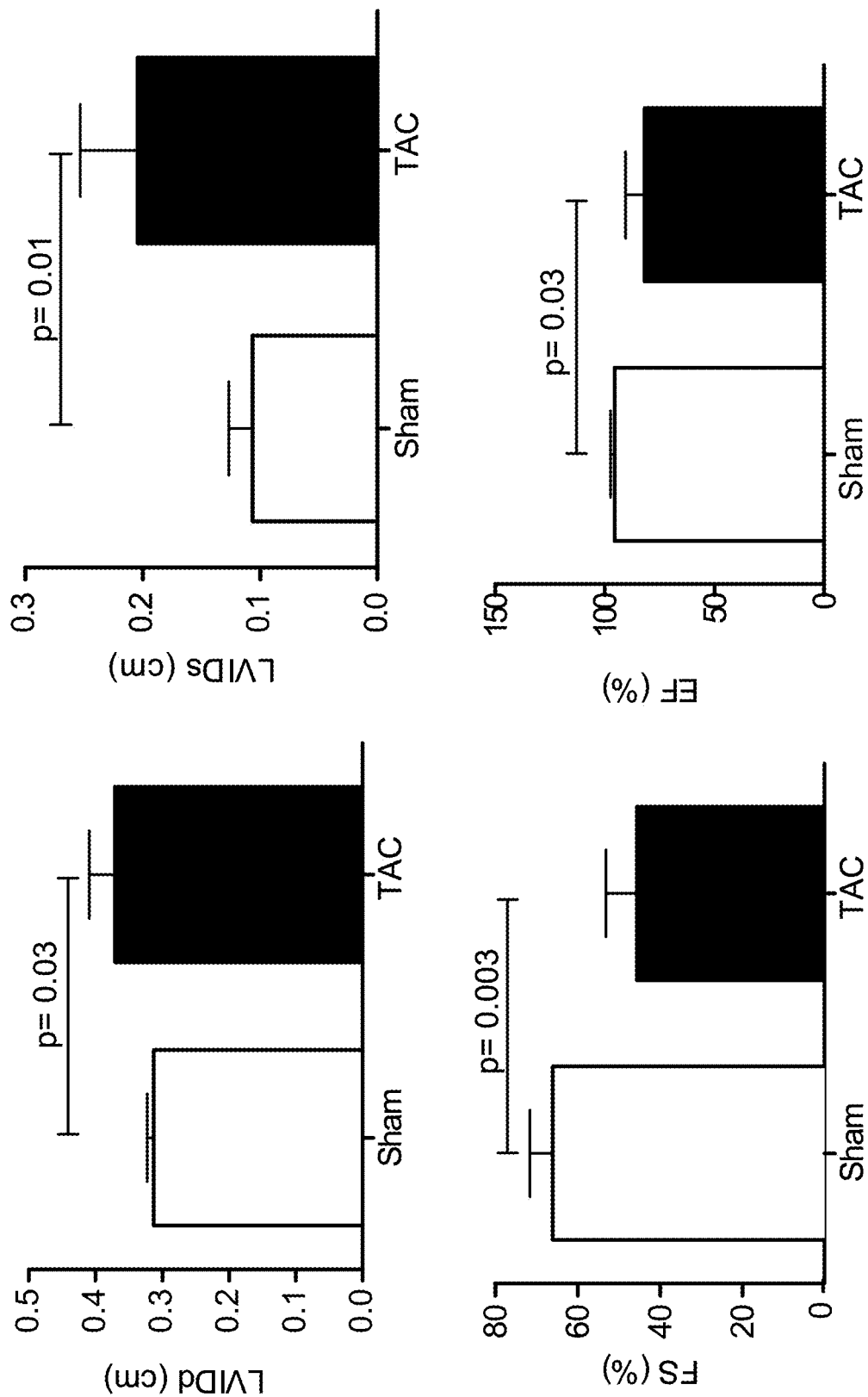
FIG. 9A depicts the characterization of TAC mice used for in vivo studies.
Figure 9B:
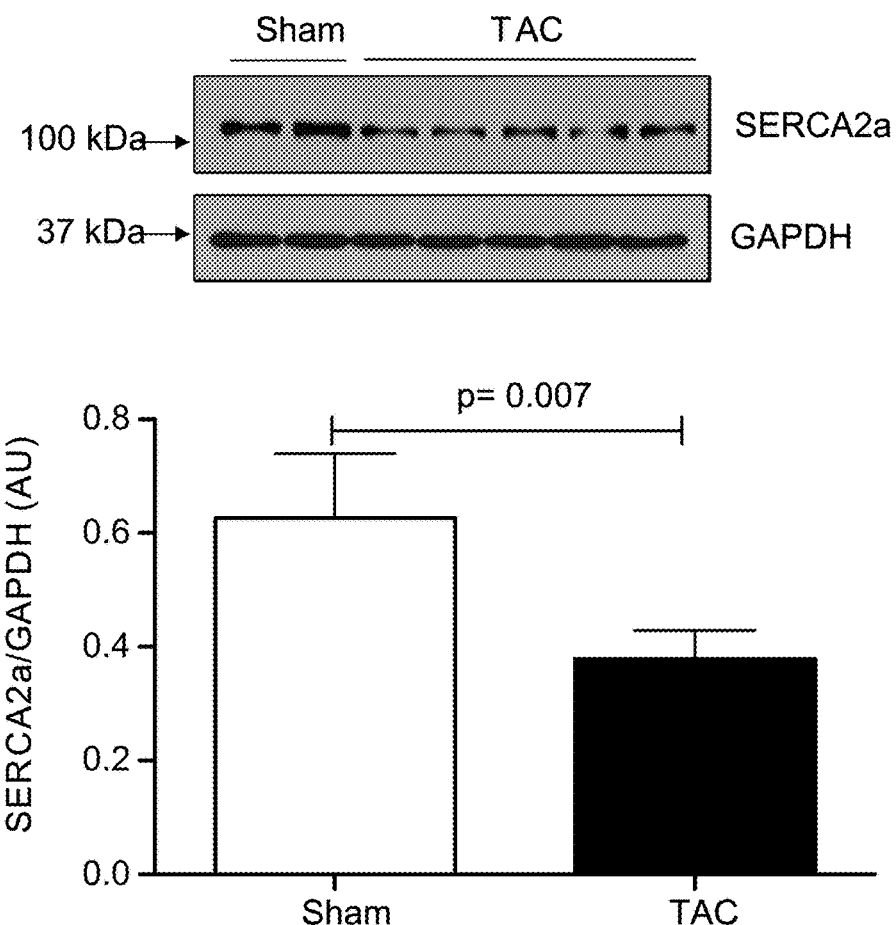
FIG. 9B depicts the effect of Example 1 on hemodynamic parameters in TAC mice.
Figure 9C:
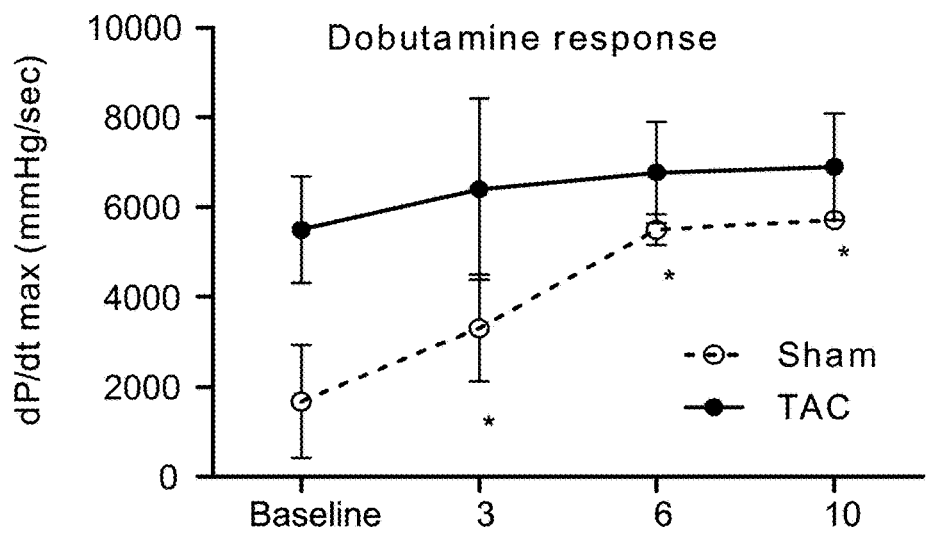
FIG. 9C depicts dobutamine response as a function of dP/dt max vs. ng/BWg in TAC mice and a sham.

Hemodynamics were measured to evaluate the acute effect of Example 1 infusion on the cardiac function of the mouse model of HF. In the first set of experiments, mice were exposed to pressure overload by thoracic aortic constriction (TAC) or sham operation and received either EXAMPLE 1 or vehicle. At two months post-TAC animals developed HF. Left ventricle (LV) was severely dilated and the cardiac function as determined by fractional shortening and ejection fraction, were significantly decreased. The sham-operated animals showed no statistically significant changes in echocardiographic parameters. The SERCA2a protein levels were significantly decreased by 40% of the normal level in TAC mice. In addition, the positive chronotropic effect of dobutamine was no longer observed in TAC mice (FIG. 9). Following cannulation of the carotid artery and external jugular vein, infusion of EXAMPLE 1 or vehicle was performed as described in Method section. Pressure and conductance catheters were introduced in the LV through the carotid artery. Pressure and volume measurements were made simultaneously and pressure volume curves were constructed as the vehicle or EXAMPLE 1 were infused.

Figure 10A:
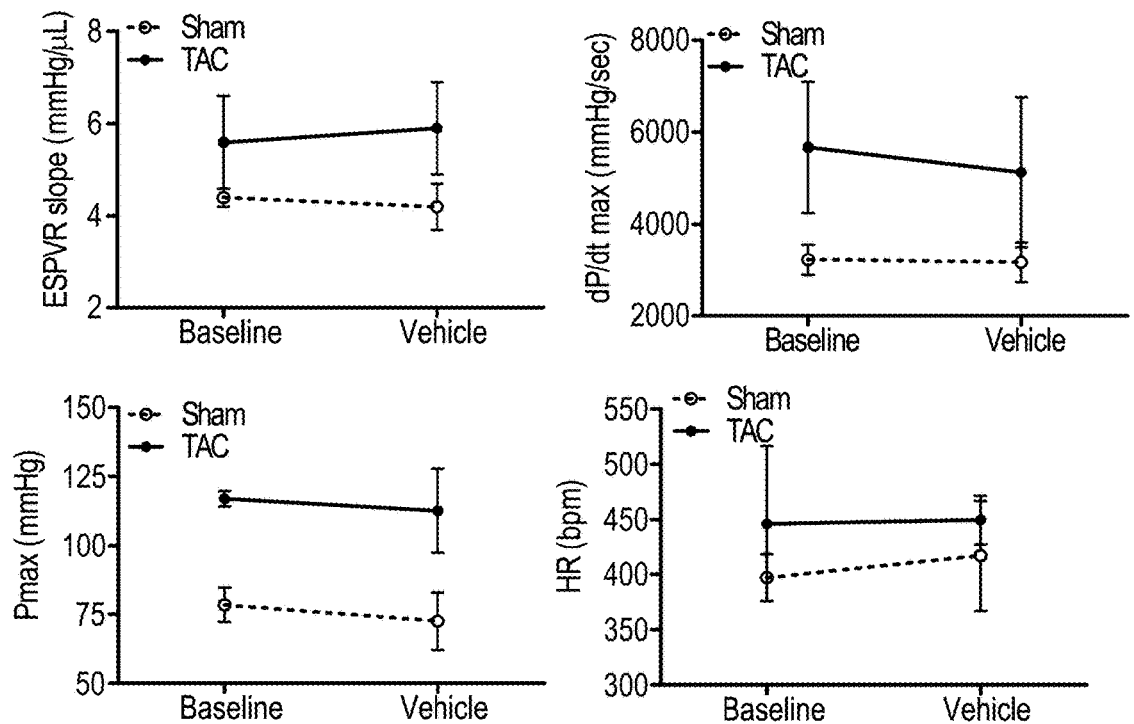
FIG. 10A depicts the effects of vehicle on hemodynamic function in sham animals.
Figure 10B:
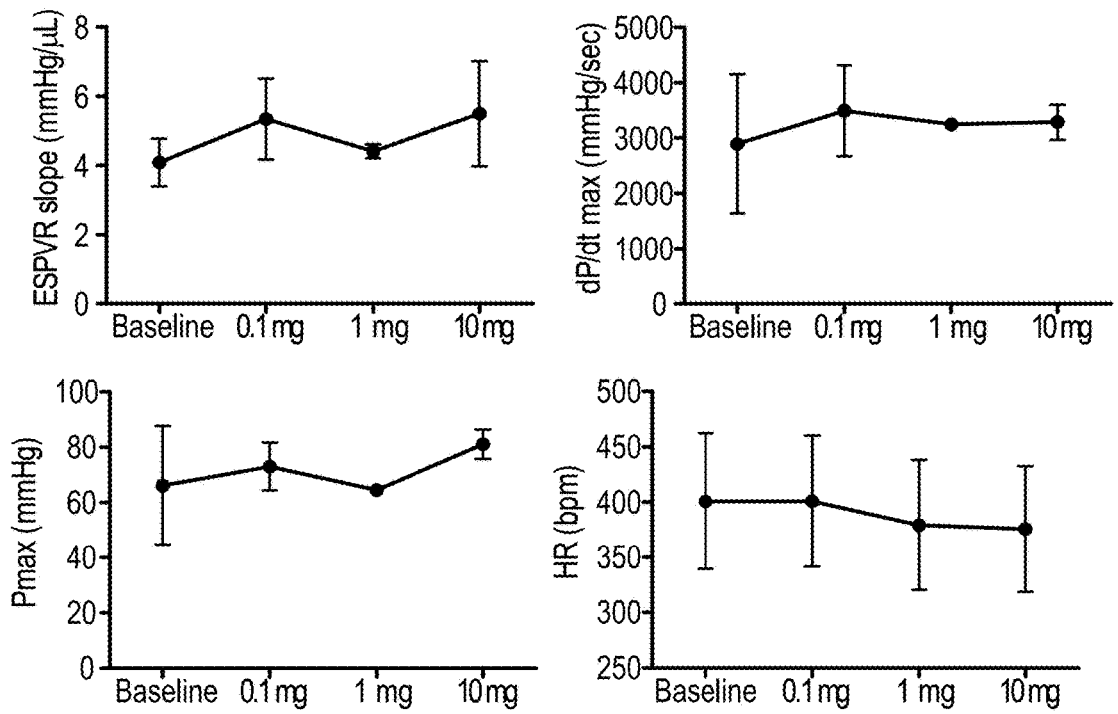
FIG. 10B depicts the effects of Example 1 on hemodynamic function in sham animals.

Hemodynamic data were obtained in 1 mg of EXAMPLE 1-treated failing hearts at 30 min and 60 min after compound treatment. The end systolic pressure-volume relationship (ESPVR) in the LV was significantly steeper in EXAMPLE 1 treated mice than baseline (p<0.001) (FIG. 9a). In addition, the rate of LV pressure (dP/dt max) rise in EXAMPLE 1 treated mice compared to the baseline (p<0.001), suggesting increased cardiac contractility. The improvement occurred within 30 minutes after treatment and maintained for 60 minutes after treatment. More importantly, infusion of EXAMPLE 1 induces an increase in the index of contractility, ESPVR in a dose dependent manner. Higher doses of EXAMPLE 1 induced a higher increase in ESPVR. The effects of EXAMPLE 1 on various hemodynamic parameters are shown in FIG. 9b and Table S1. dP/dt max increased with increasing concentration of EXAMPLE 1 while Tau a parameter of relaxation decreased an indication of enhanced relaxation. The vehicle infusion induces no change in the pressure volume relationship and does not affect the index of contractility, ESPVR and dP/dt max in both sham and TAC mice (FIG. 10a). No statistically significant changes in hemodynamic parameters were observed in sham-operated groups treated with EXAMPLE 1 (FIG. 10b).

TABLE S1

Hemodynamic parameters in 2 months after TAC animals treated with Example 1.

| Parameters | Baseline | TAC + Example 1 (n = 5 each group) | | |
| --- | --- | --- | --- | --- |
| | | 0.1 mg/kg | 1.0 mg/kg | 10 mg/kg |
| ESPVR slope (mmHg/A) | 3.1 ± 0.3 | 9.0 ± 0.8* | 11.2 ± 3.1* | 20.3 ± 1.3* |
| +dP/dt Max (mmHg/sec) | 4738.7 ± 284.1 | 4803.3 ± 290.2 | 5448.8 ± 465.1* | 6229.4 ± 357.6* |
| Pmax (mmHg) | 111.1 ± 6.4 | 115.1 ± 4.4 | 123.6 ± 18.3* | 124.5 ± 14.7* |
| Tau(1/2) (msec) | 7.7 ± 0.4 | 7.5 ± 0.5 | 6.4 ± 0.5* | 6.2 ± 0.4* |
| HR (bpm) | 422.1 ± 35.5 | 417.1 ± 15.7 | 422.3 ± 13.1 | 455.1 ± 19.4* |

ESPVR (end systolic pressure volume relationship), +dP/dt Max (peak rate of pressure rise), Pmax (maximal pressure), Tau(1/2) (relaxation time constant), HR (heart rate) in mice subjected to TAC (transverse aorta constriction) with different dose of the Example 1.
Data are given as means ± SD.
*, P < 0.05 by Student's t-test, versus Baseline.

Example F. Effects of Example 1 on Serca2 Knockout Mice

Figure 11A:
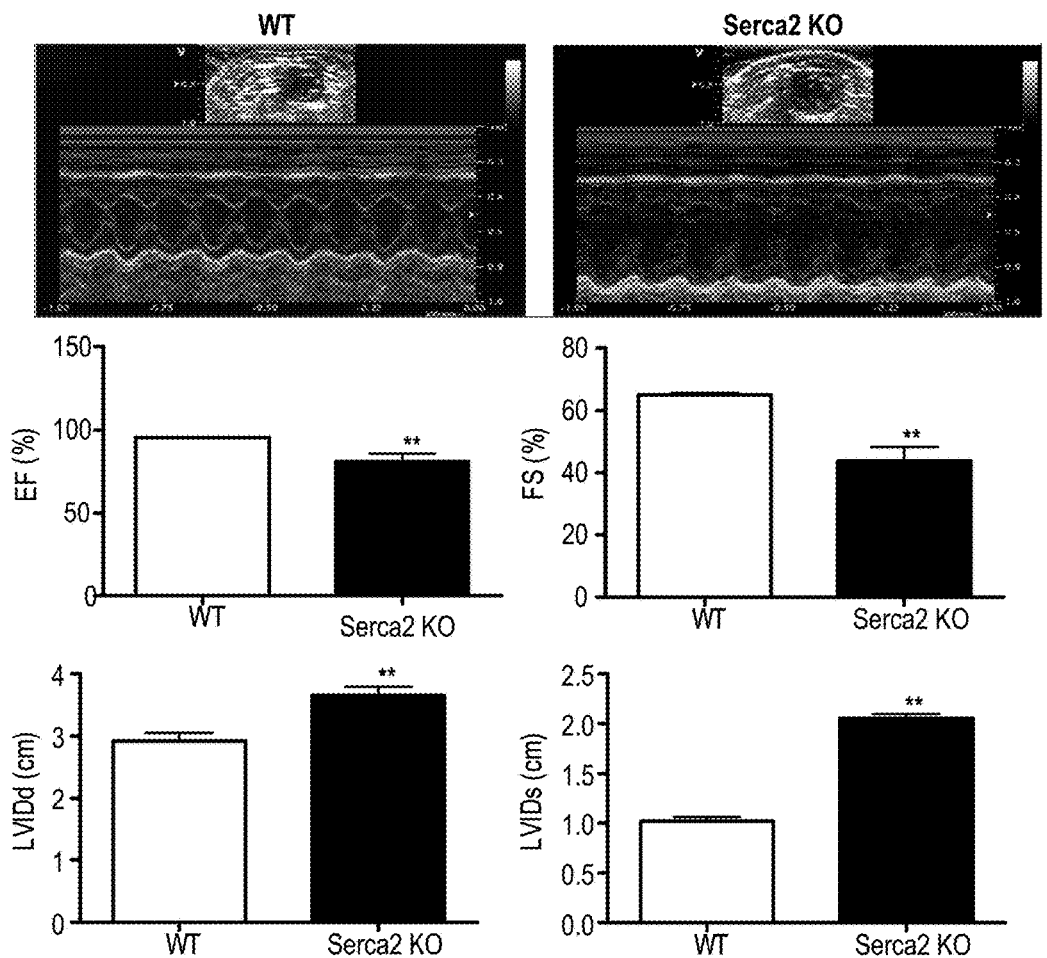
FIG. 11A depicts the animal characterization of Serca2 knockout mice.
Figure 11B:
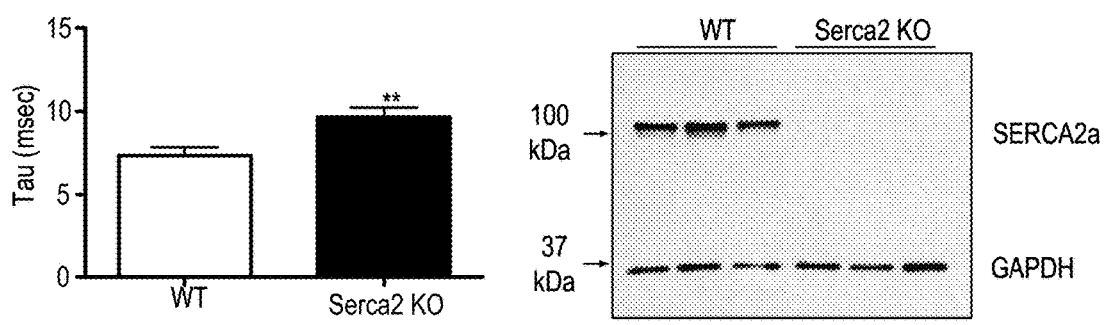
FIG. 11B depicts a bar graph and blot of control WT and Serca2 knockout mice.

Adult mice with an inducible cardiomyocyte-specific excision of the Atp2a2 (Serca2) gene (Serca2 KO) were used. Four weeks after induction of Serca2 gene excision, the mice display a substantial reduction in systolic and diastolic function (FIG. 11a). Ejection fraction was significantly lower in Serca2 KO mice compared with wild-type (WT) control (Serca2 KO, 80.90±0.23%; WT, 95.4±0.23%, p<0.001). LV fractional shortening was significantly decreased in Serca2 KO mice (Serca2 KO, 43.80±9.16%; WT, 65.04±0.59%, p<0.001). LV dimension, as measured by LVIDd and LVIDs, were significantly (p<0.001) increased. The decay constant, tau value was nearly 1.3-fold (Serca2 KO, 9.66±0.57 sec; WT, 7.33±0.5 sec, p<0.001) larger in Serca2 KO mice compared with WT control (FIG. 11b). The expression of SERCA2a was completely lacking in Serca2 KO mice (FIG. 11c).

Figure 6A:
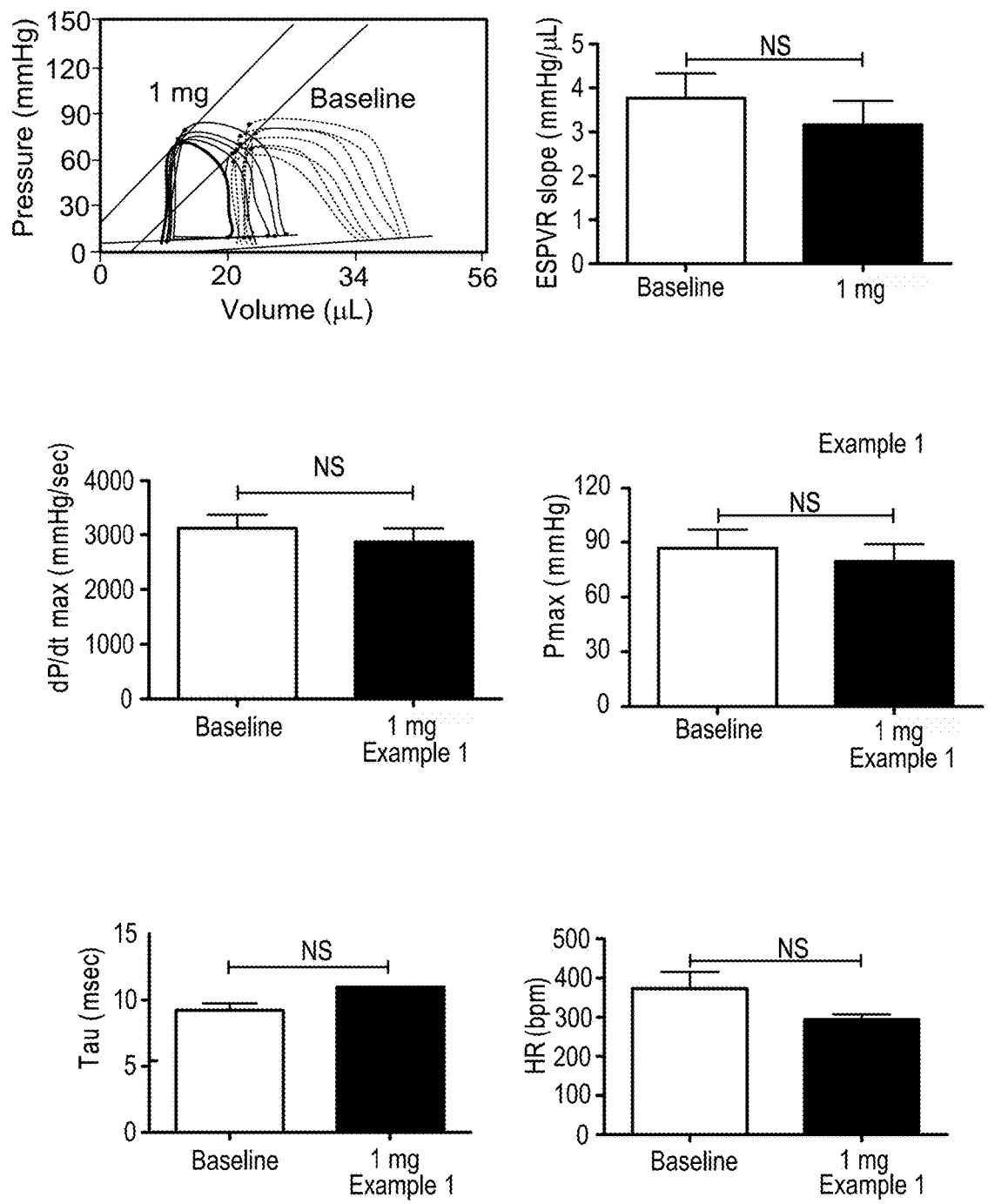
FIG. 6A depicts effects of Example 1 on hemodynamic parameters in a Serca2 knock-out mouse model.
Figure 6B:
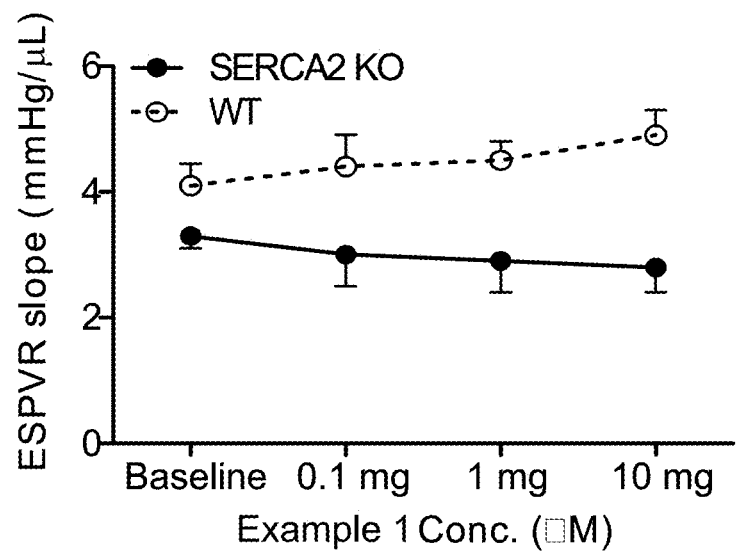
FIG. 6B depicts dose-dependent enhancement of cardiac contractility of Example 1 in a Serca2 knock-out mouse model.
Figure 6B:
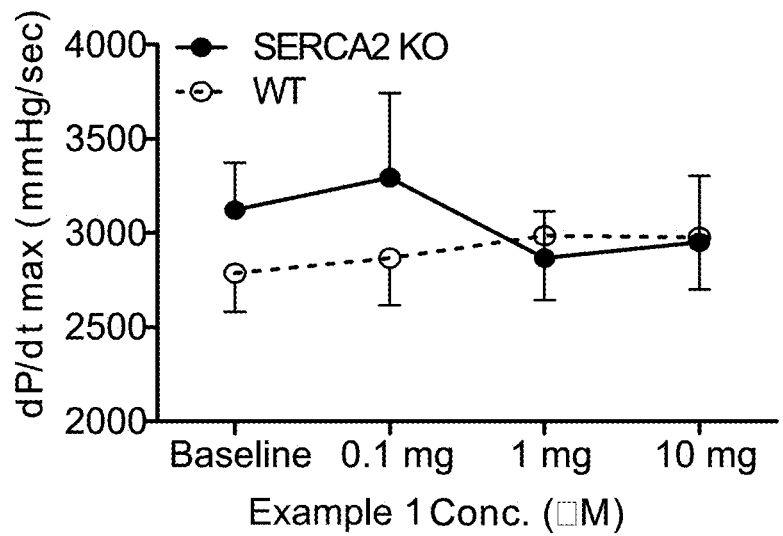

Hemodynamic parameters obtained before and after infusion of Example 1 were compared. As shown in FIG. 6, Example 1 did not induce any improvements in hemodynamic parameters in Serca2 KO mice. ESPVR slope (p=0.17, versus baseline), dP/dt max (p=0.28. versus baseline), Pmax (p=0.66 versus baseline), Tau (p=0.10 versus baseline), and heart rate (p=0.06 versus baseline) were not statistically significant difference (FIG. 6a). The dose-dependent enhancement of cardiac contractility disappeared in Serca2 KO mice (FIG. 6b).

Example G. Pharmacokinetic Profile of Example 1

Figure 12:
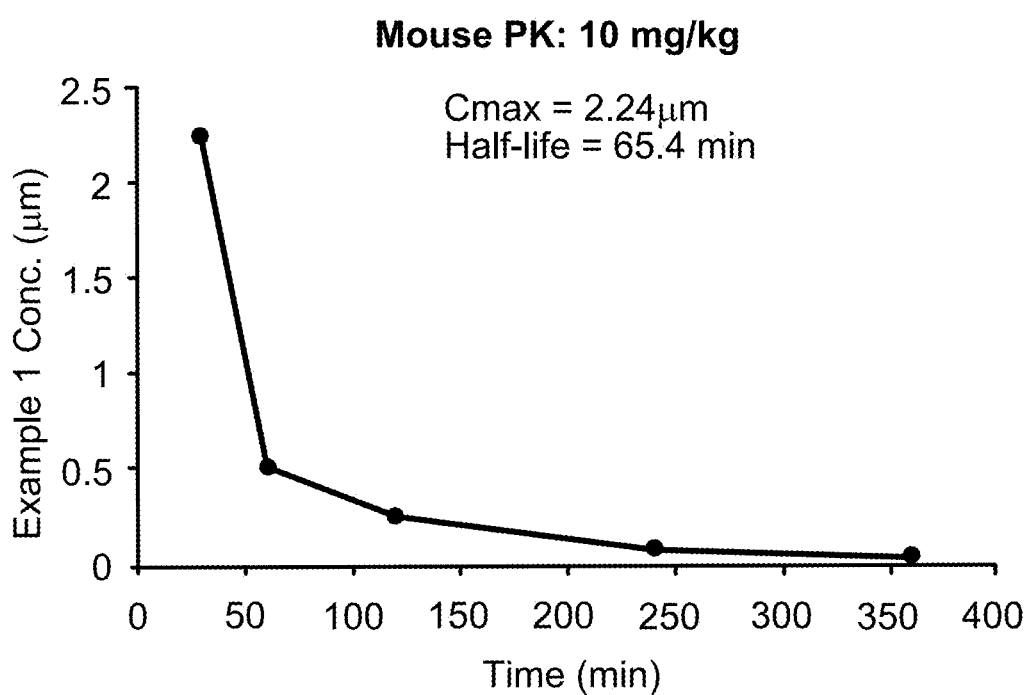
FIG. 12 depicts the pharmacokinetic analysis of the compound of Example 1 in mice at a 10 mg/kg intraperitoneal dose.

In a murine model, the half-life of Example 1 is 65.4 minutes with a Cmax of 2.24 µM (FIG. 12).

Example H. Cancer Cell Line Screen for Example 1

Figure 13:
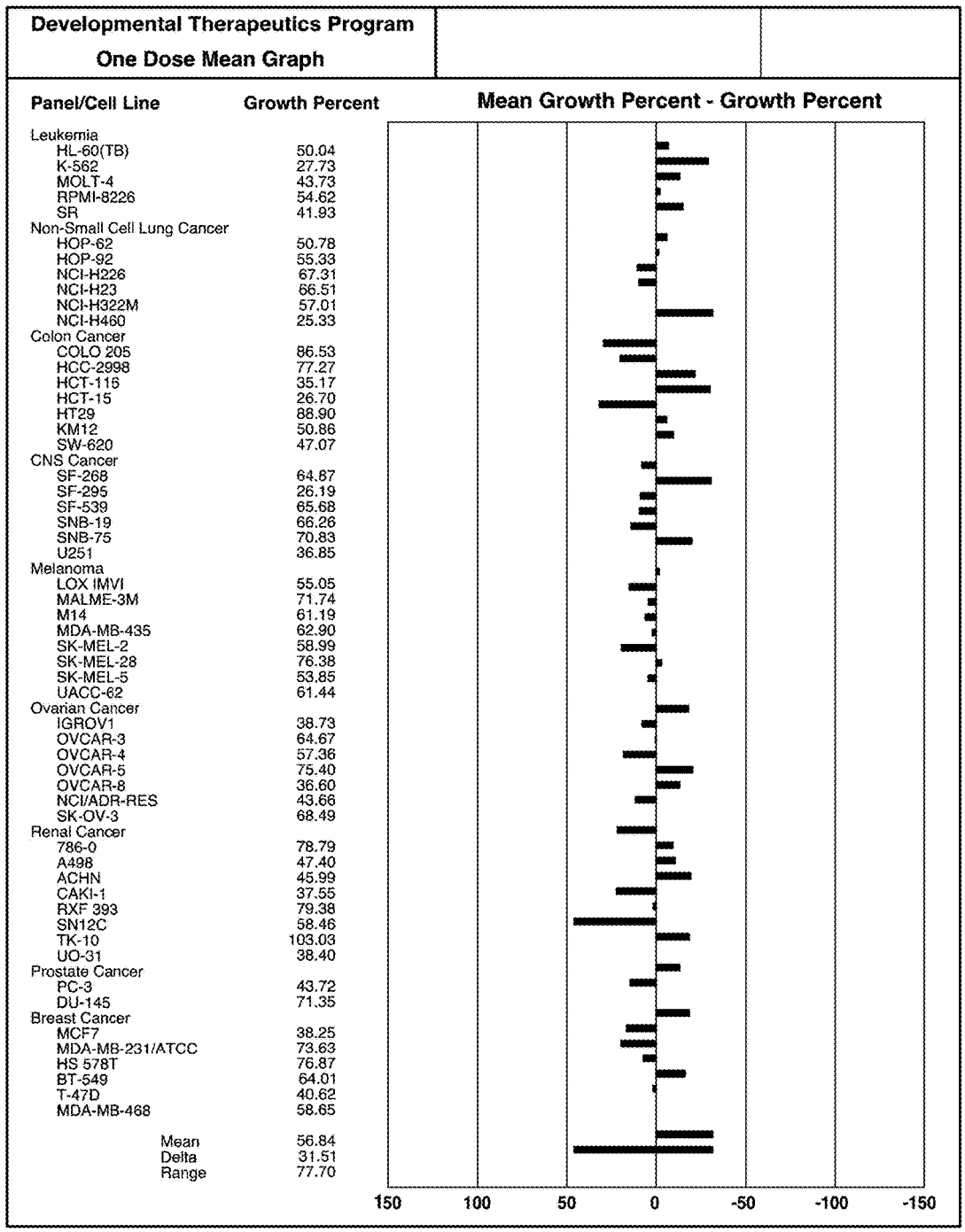
FIG. 13 depicts the effects of Example 1 in a cancer cell line panel.

The NCI-60 human tumor cell screen used by the National Cancer Institute's Developmental Therapeutics Program was performed on Example 1. The NCI-60 set includes leukemia, lymphomas, and carcinomas of ovarian, renal, breast, prostate, colon, lung and CNS origin. The results of the screen revealed that Example 1 did not induce cancer cell growth and proliferation (FIG. 13).

Example I. Effect of Examples 1-4 on SUMOylation

Figure 14:
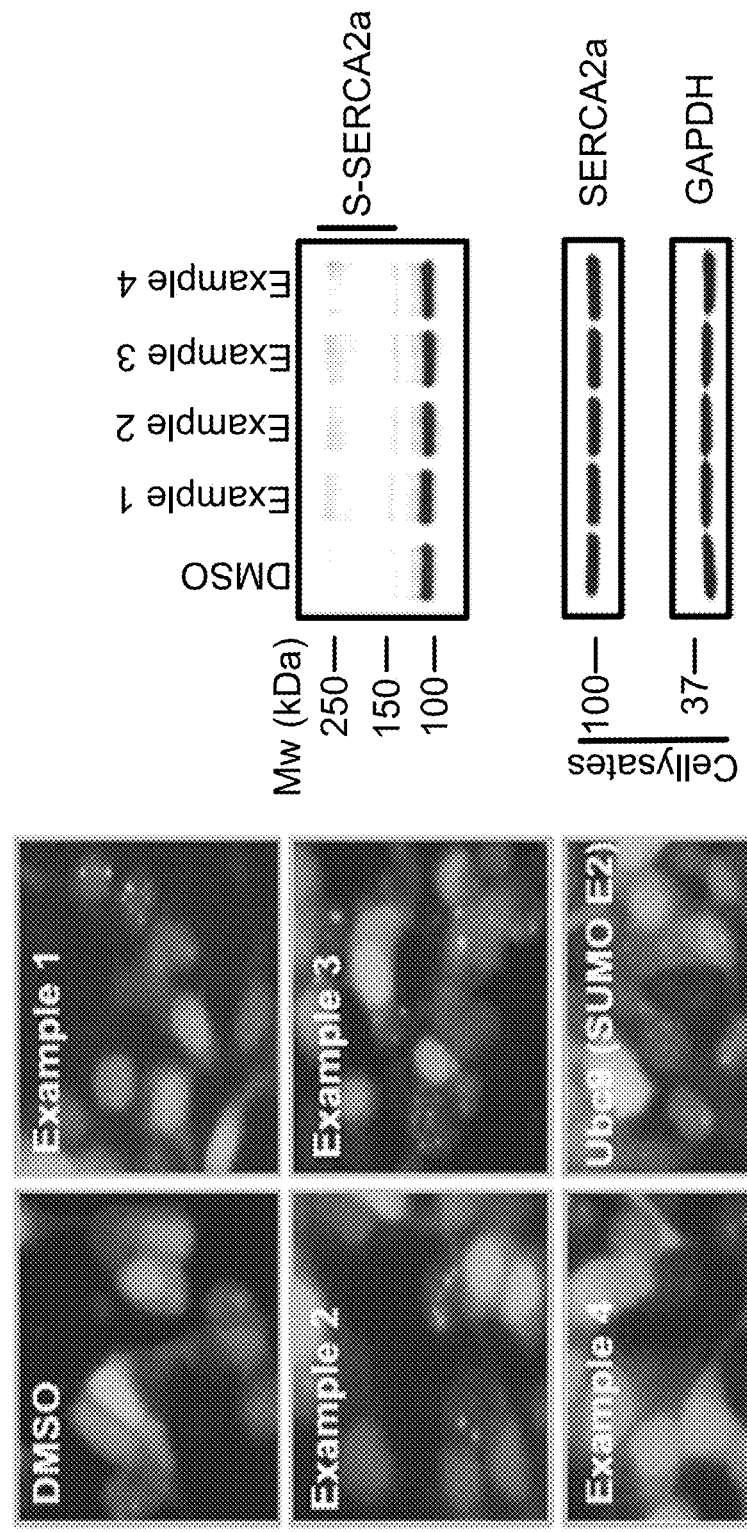

Referring to FIG. 14, Examples 1-4 induce accumulation of SUMO1 in the nucleus indication of a positive screen. Examples 1-4 also induce SERCA2a SUMOylation in HEK 293 cells.

Example J. Effect of Example 1 at Different Doses on SUMOylation

Figure 15:
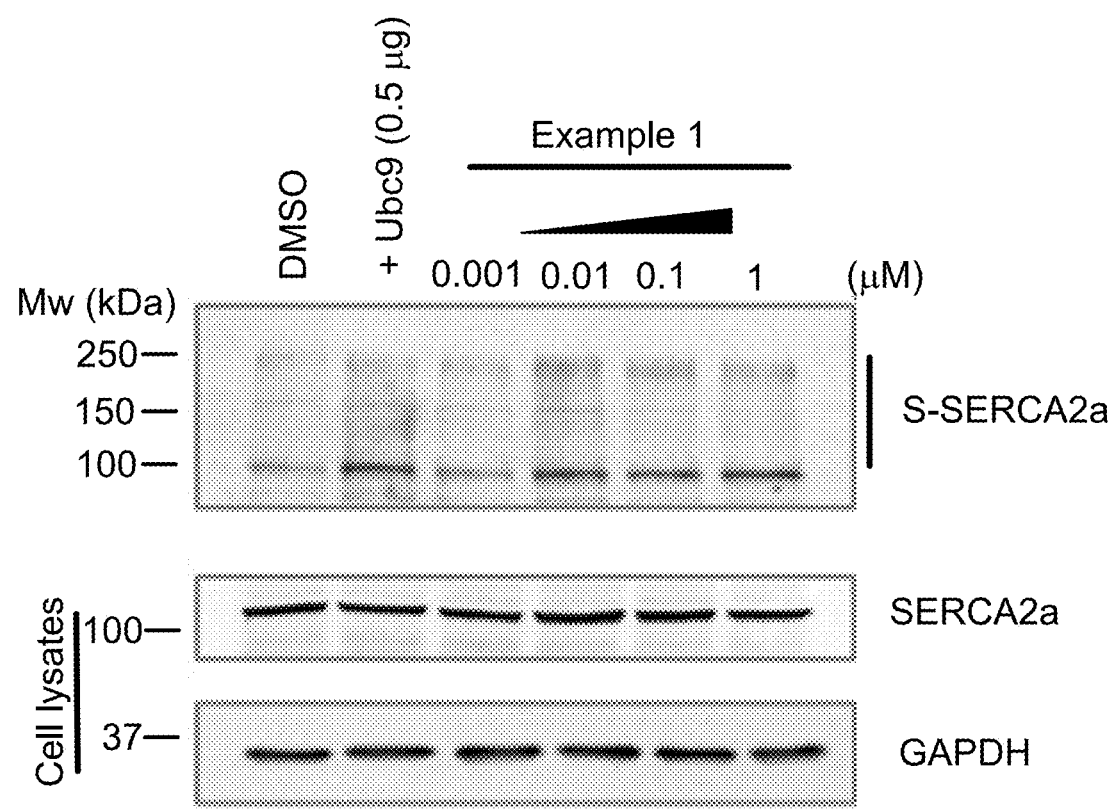
FIG. 15 depicts the effects of Example 1 on SERCA2a SUMOylation at varying doses.

Referring to FIG. 15, Example 1 increases SUMOylation of SERCA2a in a dose dependent manner.

Example K. Effect of Example 1 in a Mouse Heart Failure Model

Figure 16:
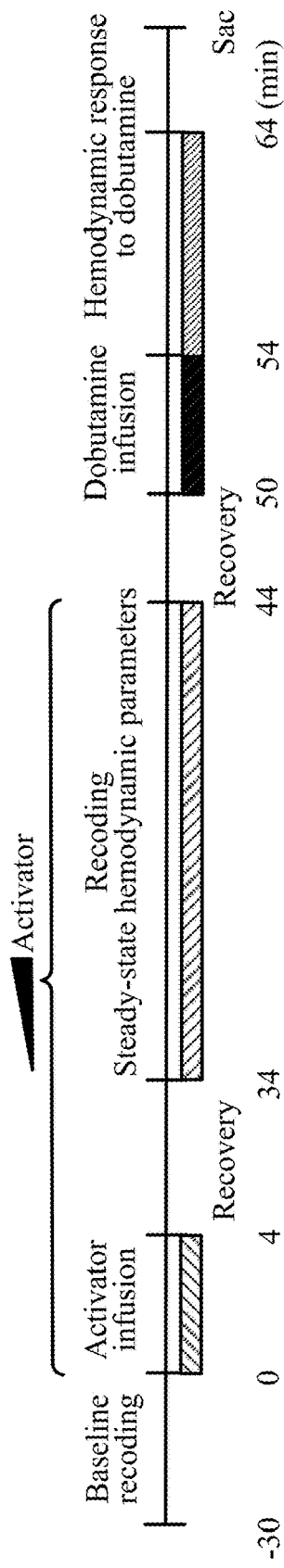
FIG. 16 depicts the protocol for hemodynamic study.

A model of heart failure was created by transaortic constriction in the mouse for 6-8 weeks. Following cannulation of the carotid artery and external jugular vein, infusion of Example 1 or vehicle was performed as shown in the protocol in FIG. 16. Pressure and conductance catheters were introduced in the left ventricle through the carotid artery. Pressure and volume measurements were made simultaneously and pressure volume curves were constructed as the vehicle or Example 1 was infused.

Figure 17:
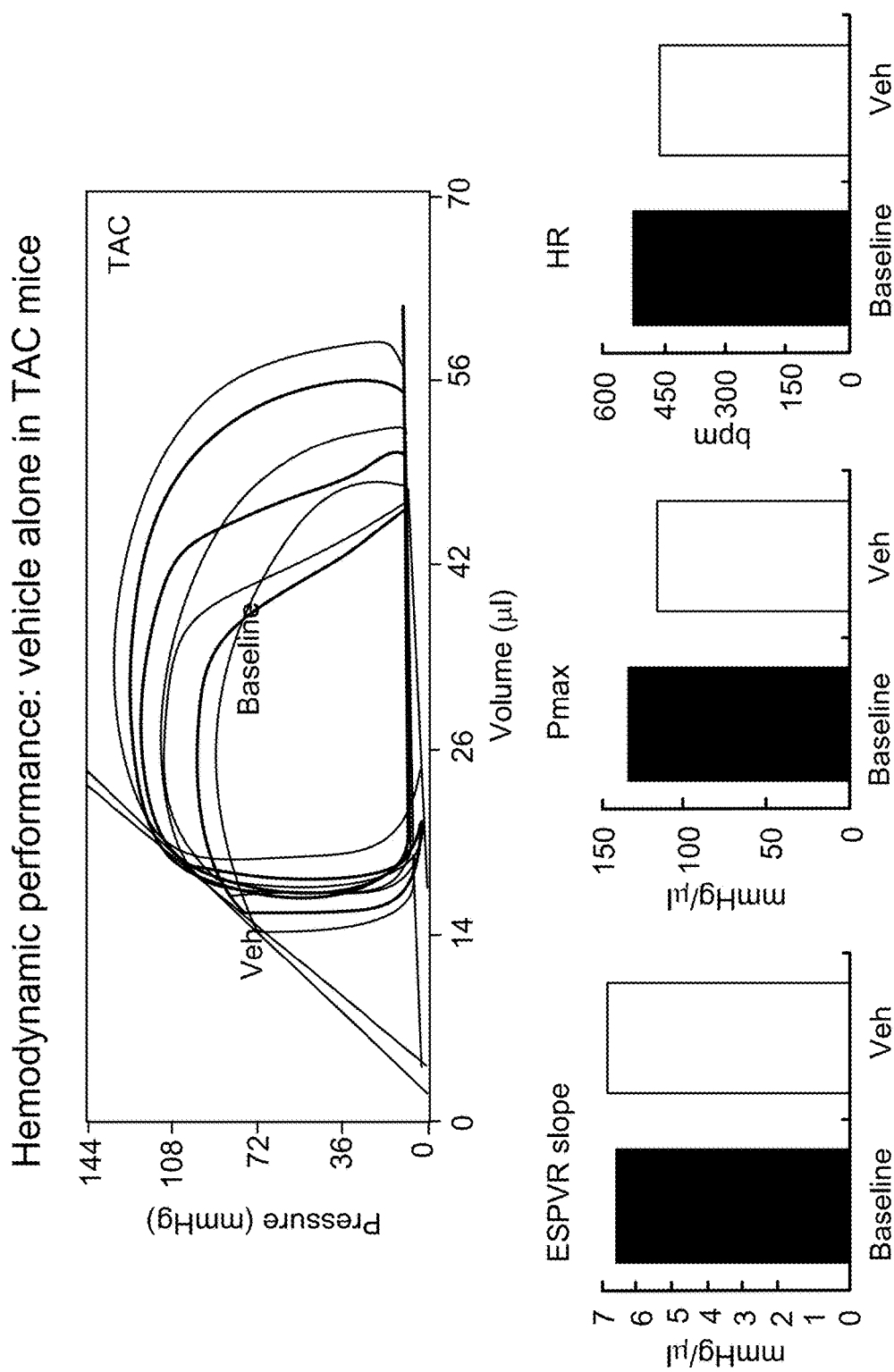
FIG. 17 depicts the pressure-volume relationships in TAC mice with increasing concentrations of vehicle.

As shown in FIG. 17, vehicle infusion induces no change in the pressure volume relationship and does not affect the index of contractility end-systolic pressure volume relationship (ESPVR).

Figure 18:
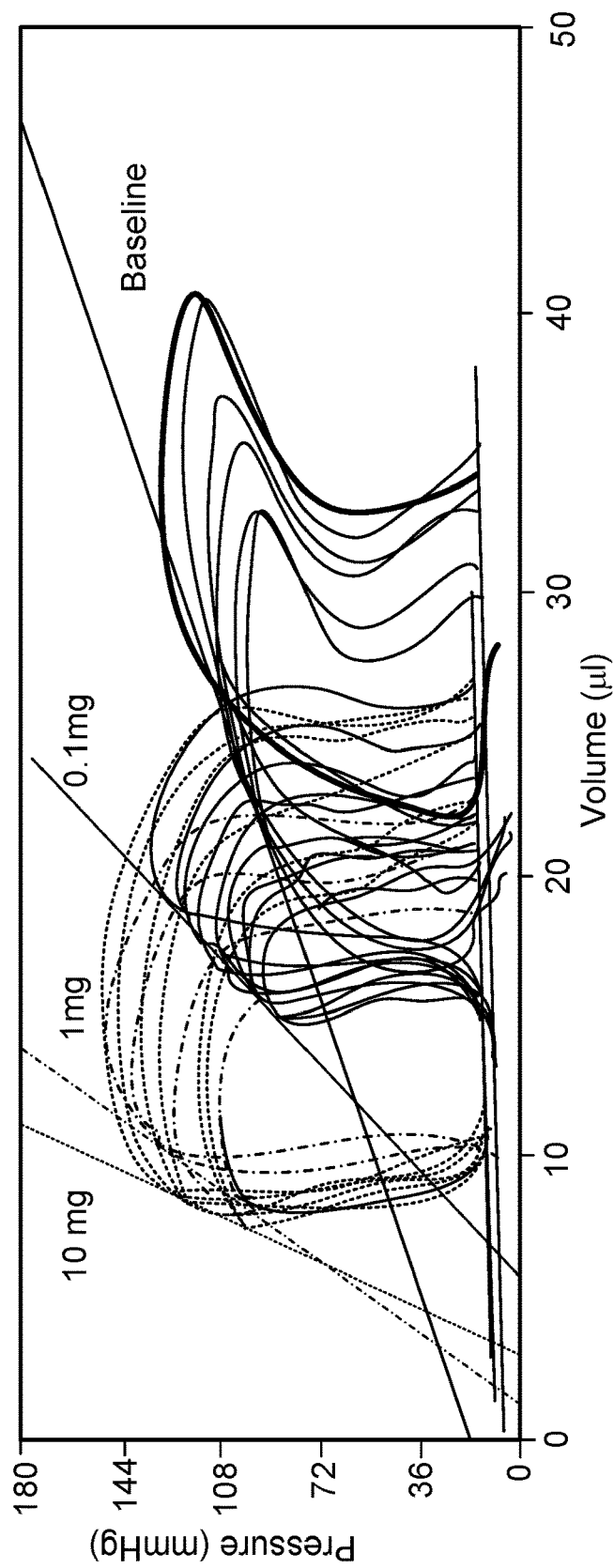
FIG. 18 depicts the pressure-volume relationships in TAC mice with increasing concentrations of Example 1.

As shown in FIG. 18, infusion of Example 1 induces an increase in the index of contractility ESPVR in a dose dependent fashion. Higher doses of Example 1 induced a higher increase in ESPVR.

Figure 19:
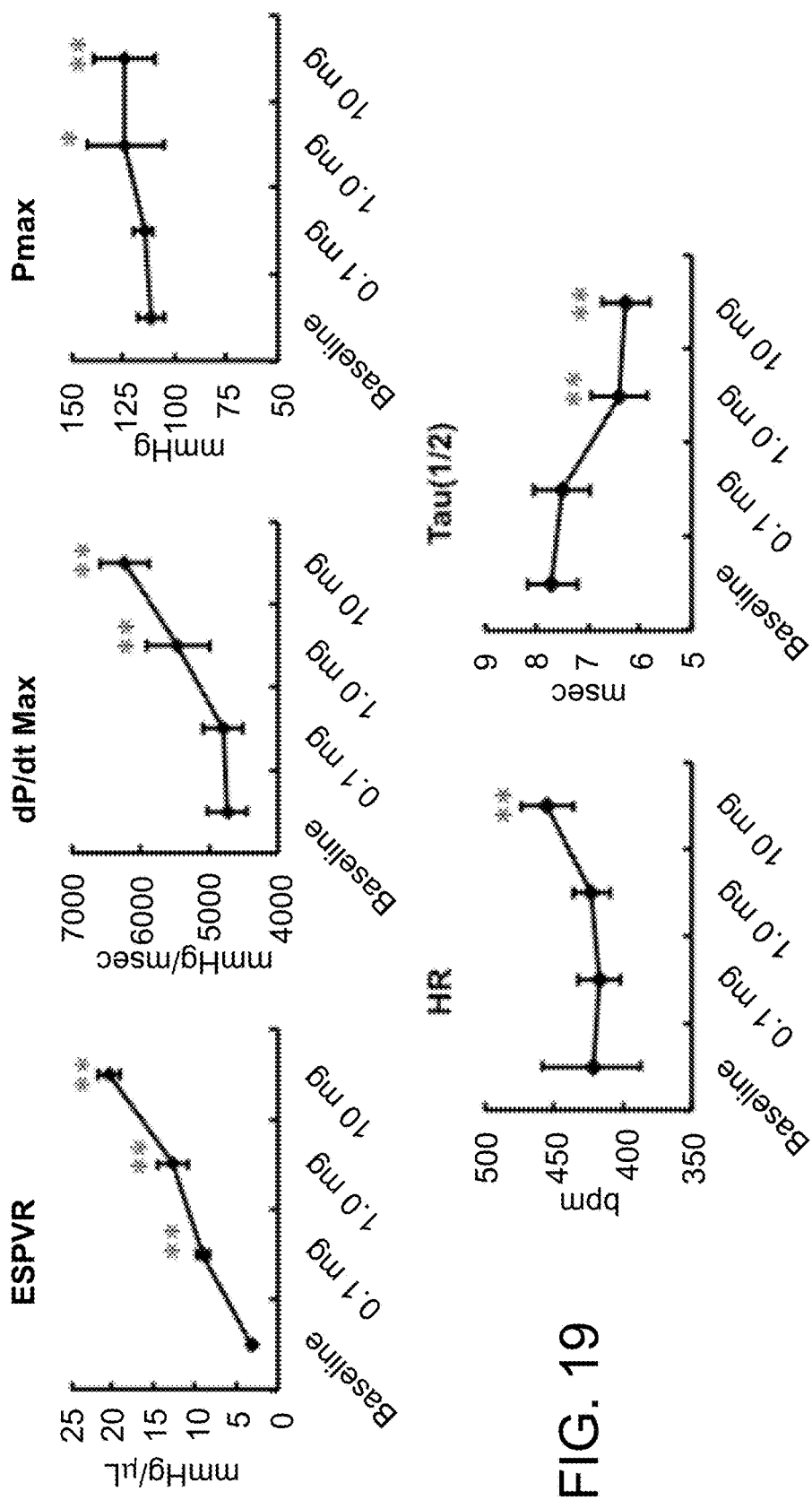
FIG. 19 depicts the effects of Example 1 on various hemodynamic parameters.

The effects of Example 1 on various hemodynamic parameters are shown in FIG. 19. Example 1 increased various hemodynamic parameters in a concentration dependent fashion. dP/dtmax increased with increasing concentration of Example 1 while Tau, a parameter of relaxation, decreased, an indication of enhanced relaxation.

Example L. Effect of Example 1 in a Non-Rodent Heart Failure Model

Figure 20:
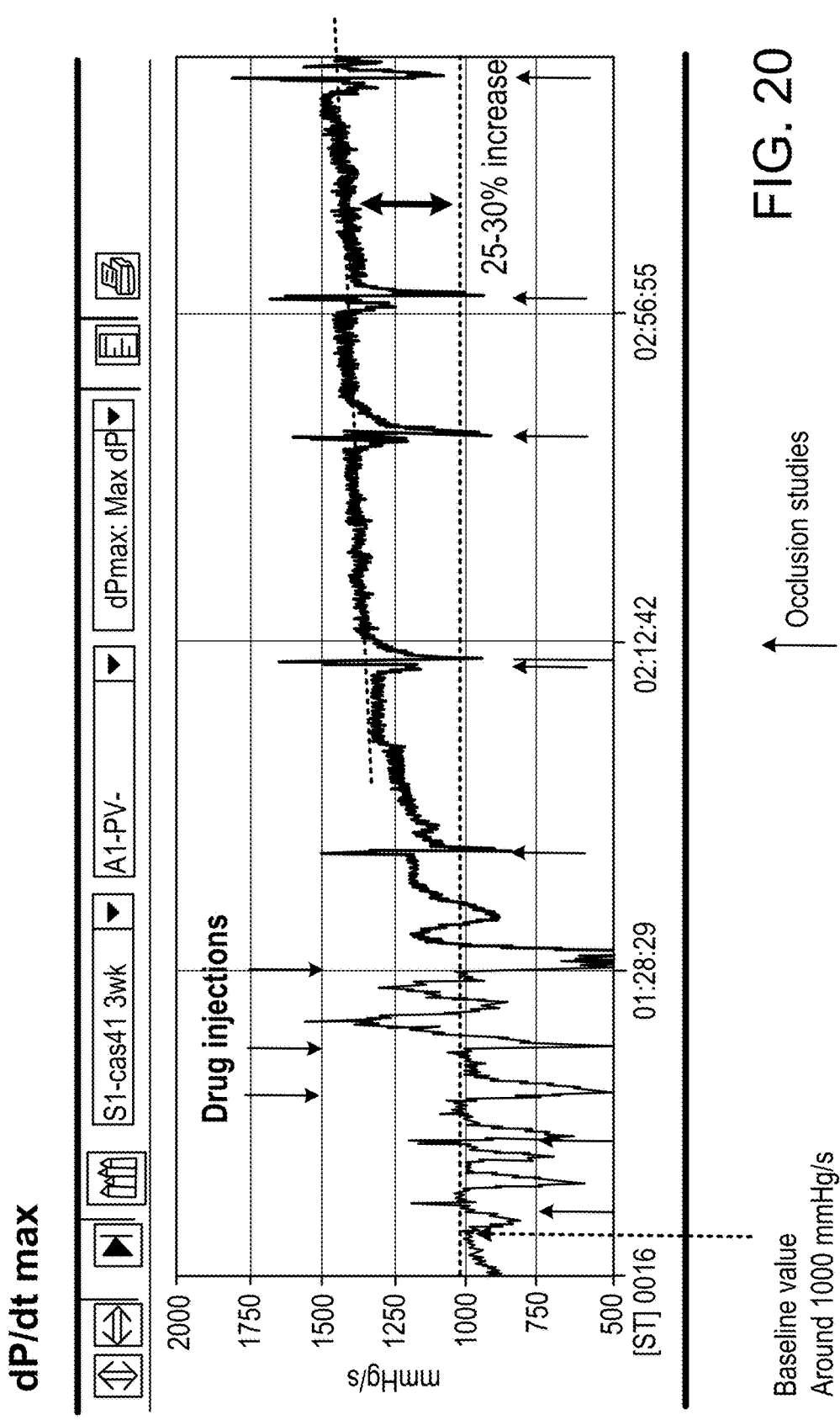
FIG. 20 depicts the effects of Example 1 on contractility in a pig as determined by dP/dt.

Example 1 was dosed in Yorkshire pigs at 5 mg/kg with severe heart failure secondary to myocardial infarction. Referring to FIG. 20, infusion of Example 1 induced an increase in contractility (as measured by dP/dt) by 25-30%.

Experimental Protocol for Pig Study

Animal

The experimental protocols complied with the National Institutes of Health Guide for the Care and Use of Laboratory Animals and standards of United States regulatory agencies. They were approved by the Institutional Animal Care and Use Committee of the Mount Sinai School of Medicine. Yorkshire pigs were pre-medicated using intramuscular Telazol™ (8.0 mg/kg; tiletamine hydrochloride and zolazepam hydrochloride; Fort Dodge Animal Health, Fort Dodge, Iowa). After the placement of an intravenous line, animals were intubated and ventilated with 100% oxygen. General anesthesia was maintained with intravenous propofol (8-10 mg/kg/hr) throughout the procedure.

Myocardial Infarction (MI) Creation

The animals underwent a 2-hour balloon occlusion of the proximal LAD (left anterior descending coronary artery) followed by reperfusion. Ten minutes before MI creation a continuous infusion of 20 mEq potassium acetate, 75 mg amiodarone, and 2 mg atropine was initiated to reduce ischemia related arrhythmia. In addition, a 75-mg bolus of amiodarone was administered i.m. Then, the left coronary artery was accessed with a 7 French hockey stick catheter (Cordis), and a 4-mm over-the-wire VOYAGER angioplasty catheter (Abbott) was advanced into the proximal LAD. After confirming the correct position, the balloon was inflated to 4 atm. Arterial pressure, blood oxygen saturation ($SpO_2$), and electrocardiogram were monitored closely throughout the procedure. The animals were defibrillated with 200 J, if necessary, and arterial hypotension was corrected with rapid i.v. saline infusion, if required.

Cardiac Performance Assessment

Cardiac performance was evaluated at one month after MI. A 7 French hockey stick catheter (Cordis) was advanced to the left coronary artery. After the coronary angiogram, a 0.014-inch guide wire (Abbott) was advanced into the LAD and 8-mm-long, 4.0-mm VOYAGER over-the-wire balloon (Abbott) was advanced to the proximal part of the coronary artery. The balloon was then inflated to 3-4 atm for 120 minutes followed by reperfusion. Example 1 (5 mg/kg) was administered by intracoronary injection (¾ to the left coronary artery and ¼ to the right coronary artery). Cardiac function was monitored and recorded for 3 hours after injection.

Additional embodiments of Formula (II) were tested for effects on SERCA2a SUMOylation and cardiac contractility. The results are summarized in Table 2.

TABLE 2

Cardiac effects of some embodiments of Formula (II).

| ID | Structure | Solubility/ Toxicity | YFP accumulation | SERCA2a SUMOylation | Cardiac Contraction |
|---|---|---|---|---|---|
| Example 2 | (structure) | 10 mM in DMSO/ Non-toxic | Active (2.93x increase vs. DMSO) | Increased 1.34x compared with DMSO control | Peak shortening 2.2x compared to DMSO control |
| Example 3 | (structure) | 10 mM in DMSO/ Non-toxic | Active (2.49x increase vs. DMSO) | Increased 1.43x compared with DMSO control | Peak shortening 2.5x compared to DMSO control |
| Example 4 | (structure) | 10 mM in DMSO/ Non-toxic | Active (2.34x increase vs. DMSO) | Increased 1.4x compared with DMSO control | Peak shortening 4.3x compared to DMSO control |

TABLE 2-continued

Cardiac effects of some embodiments of Formula (II).

| ID | Structure | Solubility/ Toxicity | YFP accumulation | SERCA2a SUMOylation | Cardiac Contraction |
|---|---|---|---|---|---|
| Example 5 | (structure) | 10 mM in DMSO/ Non-toxic | Active (2.54x increase vs. DMSO) | Not statistically significant | — |
| Example 6 | (structure) | 10 mM in DMSO/ 30% | Active (2.93x increase vs. DMSO) | Not statistically significant | — |
| Example 7 | (structure) | 10 mM in DMSO/ Non-toxic | Active (2.2x increase vs. DMSO) | Not statistically significant | — |

TABLE 2-continued

Cardiac effects of some embodiments of Formula (II).

| ID | Structure | Solubility/ Toxicity | YFP accumulation | SERCA2a SUMOylation | Cardiac Contraction |
|---|---|---|---|---|---|
| Example 8 | 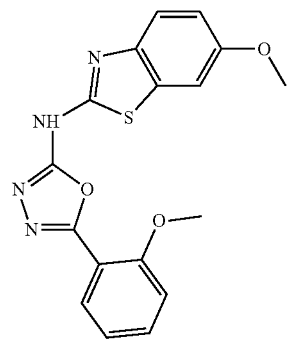 [SMILES: COc1ccc2nc(Nc3nnc(-c4ccccc4OC)o3)sc2c1] | 10 mM in DMSO/ 30% | Active (2.37x increase vs. DMSO) | Not statistically significant | — |
| Example 9 | 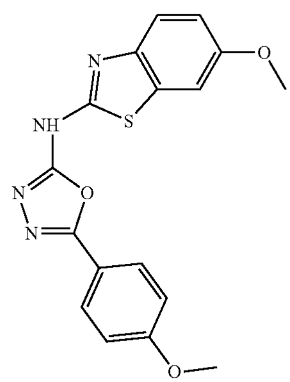 [SMILES: COc1ccc(-c2nnc(Nc3nc4ccc(OC)cc4s3)o2)cc1] | Crystallized at 2.5 mM/ Toxic | Active | Not statistically significant | — |
| Example 10 | 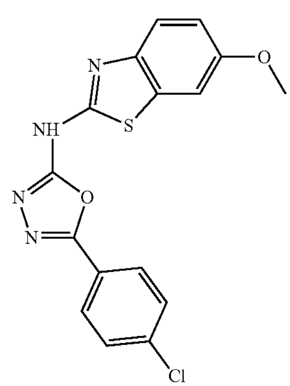 [SMILES: COc1ccc2nc(Nc3nnc(-c4ccc(Cl)cc4)o3)sc2c1] | Solubility <2.5 mM/ >50% | Active | Not statistically significant | — |
| Example 11 | 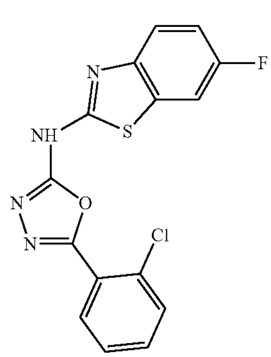 [SMILES: Fc1ccc2nc(Nc3nnc(-c4ccccc4Cl)o3)sc2c1] | Solubility <2.5 mM/ >50% | Active | Not statistically significant | — |

TABLE 2-continued

Cardiac effects of some embodiments of Formula (II).

| ID | Structure | Solubility/ Toxicity | YFP accumulation | SERCA2a SUMOylation | Cardiac Contraction |
|---|---|---|---|---|---|
| Example 12 | 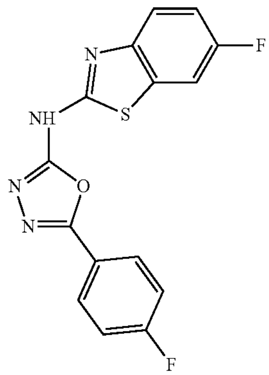 [SMILES: Fc1ccc(-c2nnc(Nc3nc4ccc(F)cc4s3)o2)cc1] | Solubility <2.5 mM/ >50% | Active | Not statistically significant | — |
| Example 13 | 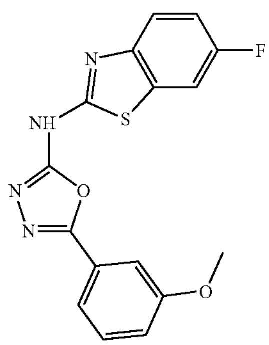 [SMILES: COc1cccc(-c2nnc(Nc3nc4ccc(F)cc4s3)o2)c1] | Solubility <2.5 mM/ >50% | Active | Not statistically significant | — |
| Example 14 | 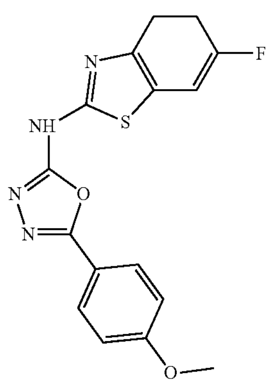 [SMILES: COc1ccc(-c2nnc(Nc3nc4c(s3)C=C(F)CC4)o2)cc1] | Solubility <2.5 mM/ >50% | Active | Not statistically significant | — |
| Example 15 | 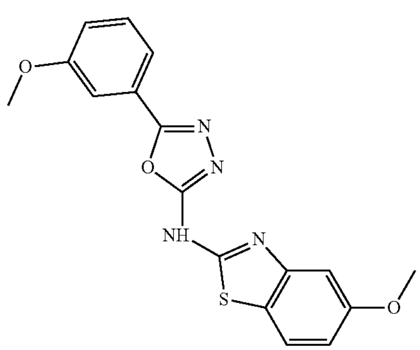 | Solubility <2.5 mM/ >50% | Active | Not statistically significant | — |

TABLE 2-continued

Cardiac effects of some embodiments of Formula (II).

| ID | Structure | Solubility/ Toxicity | YFP accumulation | SERCA2a SUMOylation | Cardiac Contraction |
|---|---|---|---|---|---|
| Example 16 | 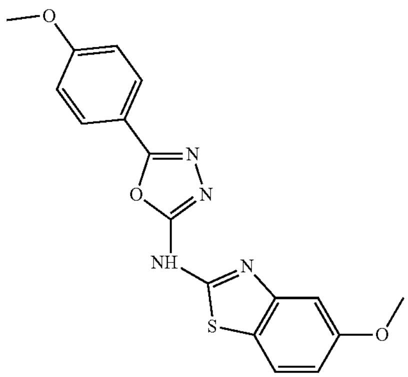 | Solubility <2.5 mM/ >50% | Active | Not statistically significant | — |
| Example 17 | 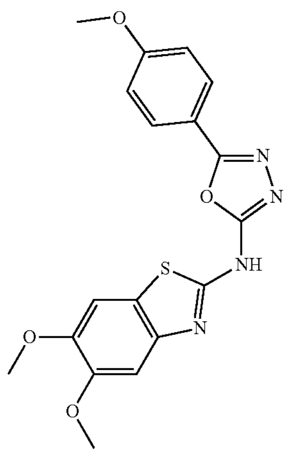 [SMILES: COc1ccc(-c2nnc(Nc3nc4cc(OC)c(OC)cc4s3)o2)cc1] | 5 mM/ Non-toxic | Active (2.2x increase vs. DMSO) | Not statistically significant | — |
| Example 18 | 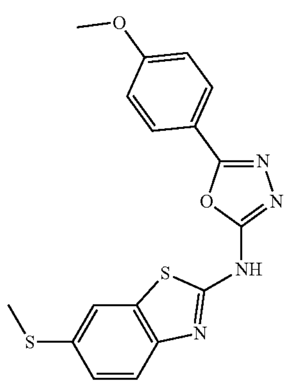 [SMILES: COc1ccc(-c2nnc(Nc3nc4ccc(SC)cc4s3)o2)cc1] | Solubility <2.5 mM/ >50% | Active | Not statistically significant | — |

What is claimed is:

1. A method of treating heart failure, cardiac hypertrophy, myocarditis, myocardial infarction, ischemia, cardiac arrhythmias, vascular rhexis, cardiac arrhythmia, valvulopathy, diastolic dysfunction, hypertension, neurodegenerative disorders, viral infection, liver disease, or inflammation in a patient in need thereof, comprising administering to said patient a therapeutically effective amount of a compound of Formula II:

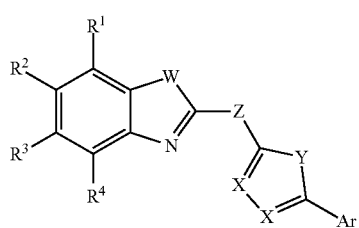

II or a pharmaceutically acceptable salt thereof; wherein:
Ar is aryl or heteroaryl, each of which is optionally substituted with 1, 2, 3, 4, 5, or 6 independently selected $R^{1a}$ groups;
W is S or O;
Y is O;
each X is N;
Z is O, S, or $NR^A$;
$R^A$ is H or $C_{1-4}$ alkyl;
$R^1$, $R^2$, $R^3$, and $R^4$ are each independently selected from hydrogen, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylamino sulfonyl, aminosulfonylamino, $C_{1-6}$ alkylaminosulfonylamino, and di-$C_{1-4}$alkylaminosulfonylamino; wherein said $C_{1-6}$ alkyl, $C_{1-6}$ haloalkyl, $C_{1-6}$ alkoxy, $C_{1-6}$ haloalkoxy, $C_{1-6}$ alkylamino, di-$C_{1-4}$-alkylamino, $C_{1-6}$ alkylcarbamyl, di($C_{1-4}$alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino;
each $R^{1a}$ is hydrogen.

2. A method according to claim 1, wherein Ar is phenyl.
3. A method according to claim 1, wherein W is S.
4. A method according to claim 1, wherein Z is NH.
5. A method according to claim 1, wherein $R^1$, $R^2$, $R^3$, and $R^4$ are independently selected from hydrogen, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, and di-$C_{1-4}$-alkylamino.
6. A method according to claim 1, wherein $R^1$, $R^2$, $R^3$, and $R^4$ are independently selected from hydrogen and $C_{1-6}$ alkoxy.
7. A method according to claim 1, wherein at least three of $R^1$, $R^2$, $R^3$, and $R^4$ are hydrogen.
8. A method of treating heart failure, cardiac hypertrophy, myocarditis, myocardial infarction, ischemia, cardiac arrhythmias, vascular rhexis, cardiac arrhythmia, valvulopathy, diastolic dysfunction, hypertension, neurodegenerative disorders, viral infection, liver disease, or inflammation in a patient in need thereof, comprising administering to said patient a therapeutically effective amount of a compound of Formula II:

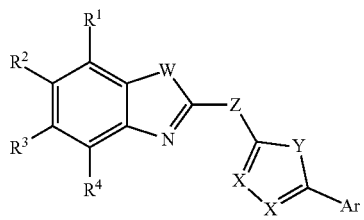

II or a pharmaceutically acceptable salt thereof; wherein:
Ar is aryl or heteroaryl, each of which is optionally substituted with 1, 2, 3, 4, 5, or 6 independently selected $R^{1a}$ groups;
W is S or O;
Y is O;
each X is N;
Z is O, S, or $NR^A$;
$R^A$ is H or $C_{1-4}$ alkyl;
$R^1$, $R^2$, $R^3$, and $R^4$ are each hydrogen;
each $R^{1a}$ is independently selected from halo, CN, nitro, hydroxy, $C_{1-6}$ alkyl, $C_{1-6}$ haloalkyl, $C_{2-6}$ alkenyl, $C_{2-6}$ alkynyl, $C_{3-7}$cycloalkyl, $C_{2-6}$ heterocycloalkyl, phenyl, $C_{1-6}$ heteroaryl, $C_{1-6}$ haloalkoxy, amino, $C_{1-6}$ alkylamino, di-$C_{1-4}$-alkylamino, carboxy, carbamyl, $C_{1-6}$ alkylcarbamyl, di($C_{1-4}$alkyl)carbamyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$alklaminosulfonyl, di-$C_{1-4}$ alklaminosulfonyl, aminosulfonylamino $C_{1-6}$ alkylaminosulfonylamino, and di-$C_{1-4}$alkylaminosulfonylamino; wherein said $C_{1-6}$ alkyl, $C_{1-6}$ haloalkyl, $C_{2-6}$ alkenyl, $C_{2-6}$ alkynyl, $C_{3-7}$ cycloalkyl, $C_{2-6}$ heterocycloalkyl, phenyl, $C_{1-6}$ heteroaryl, $C_{1-6}$ haloalkoxy, $C_{1-6}$ alkylamino, di-$C_{1-4}$-alkylamino, $C_{1-6}$ alkylcarbamyl, di($C_{1-4}$ alkyl)carbamyl, and $C_{1-6}$ alkylcarbonyl are each optionally substituted with 1, 2, or 3 groups independently selected from halo, CN, hydroxy, $C_{1-3}$ alkoxy, amino, alkylamino, and di-$C_{1-3}$-alkylamino; or
two adjacent $R^{1a}$ taken together with the atoms to which they are attached can form a 3-7 membered carbocyclic or 4-6 membered heterocyclic ring, each of which is optionally substituted with 1, 2, 3, or 4 $C_{1-3}$ alkyl groups.

9. A method according to claim 8, wherein the compound is a compound of Formula Ia:

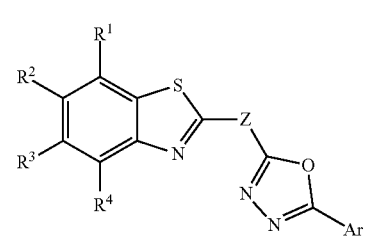

Ia or a pharmaceutically acceptable salt thereof.
10. A method according to claim 8, wherein the compound is a compound of Formula Ib:

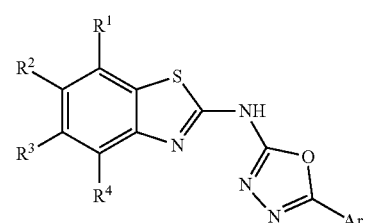

Ib or a pharmaceutically acceptable salt thereof.
11. A method according to claim 8, wherein the compound is a compound of Formula Ic:

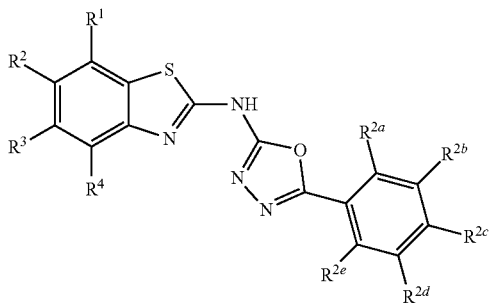

or a pharmaceutically acceptable salt thereof wherein:

$R^{2a}$, $R^{2b}$, $R^{2c}$, $R^{2d}$, and $R^{2e}$ are each independently selected from hydrogen, halo, CN, nitro, hydroxy, $C_{1-6}$ alkyl, $C_{1-6}$haloalkyl, $C_{2-6}$ alkenyl, $C_{2-6}$ alkynyl, $C_{3-7}$cycloalkyl, $C_{2-6}$ heterocycloalkyl, phenyl, $C_{1-6}$ heteroaryl, $C_{1-6}$haloalkoxy, amino, $C_{1-6}$alkylamino, carboxy, carbamyl, $C_{1-6}$alkylcarbamyl, di($C_{1-4}$alkyl)carbamyl, $C_{1-6}$ alkylcarbonyl, $C_{1-6}$alkoxycarbonyl, $C_{1-6}$alkylcarbonyloxy, $C_{1-6}$alkylsulfonyl, $C_{1-6}$alkylcarbonylamino, $C_{1-6}$ alkylsulfonylamino, aminosulfonyl, $C_{1-6}$alkylaminosulfonyl, di-$C_{1-4}$ alkylaminosulfonyl, aminosulfonylamino, $C_{1-6}$alkylaminosulfonylamino, and di-$C_{1-4}$ alkylaminosulfonylamino; wherein said $C_{1-6}$ alkyl, $C_{1-6}$haloalkyl, $C_{2-6}$ alkenyl, $C_{2-6}$ alkynyl, $C_{3-7}$cycloalkyl, $C_{2-6}$ heterocycloalkyl, phenyl, $C_{1-6}$heteroaryl, $C_{1-6}$ haloalkoxy, $C_{1-6}$ alkylamino, di-$C_{1-4}$-alkylamino, $C_{1-6}$alkylcarbamyl, di($C_{1-4}$alkyl)carbamyl, and $C_{1-6}$ alkylcarbonyl are each optionally substituted with 1, 2, or 3 groups independently selected from halo, CN, hydroxy, $C_{1-3}$ alkoxy, amino, $C_{1-3}$ alkylamino, and di-$C_{1-3}$-alkylamino.

12. A method according to claim 11, wherein $R^{2a}$, $R^{2b}$, $R^{2c}$, $R^{2d}$, and $R^{2e}$ are each independently selected from hydrogen, halo, CN, hydroxy, $C_{1-6}$ alkyl, $C_{1-6}$ haloalkyl, and $C_{1-6}$ haloalkoxy.

13. A method of treating heart failure, cardiac hypertrophy, myocarditis, myocardial infarction, ischemia, cardiac arrhythmias, vascular rhexis, cardiac arrhythmia, valvulopathy, diastolic dysfunction, hypertension, neurodegenerative disorders, viral infection, liver disease, or inflammation in a patient in need thereof, comprising administering to said patient a therapeutically effective amount of 5-(4 chlorophenyl)-N-(6-methoxybenzo[d]thiazol-2-yl)-1,3,4-oxadiazol-2-amine, or a pharmaceutically acceptable salt thereof.

14. A method according to claim 1, wherein said heart failure is selected from congestive heart failure (CHF), chronic heart failure, and ischemic heart failure.

15. A method according to claim 8, wherein the compound is a compound of Formula IIc:

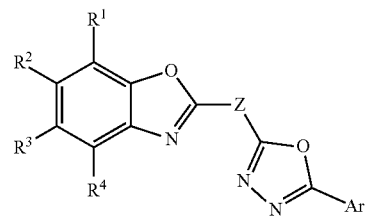

or a pharmaceutically acceptable salt thereof.

16. A method according to claim 8, wherein the method further comprises administering to the patient an adeno-associated vector (AAV) comprising SERCA2a.

* * * * *

UNITED STATES PATENT AND TRADEMARK OFFICE
CERTIFICATE OF CORRECTION

PATENT NO. : 10,501,453 B2
APPLICATION NO. : 15/826238
DATED : December 10, 2019
INVENTOR(S) : Russell Dahl et al.

Page 1 of 2

It is certified that error appears in the above-identified patent and that said Letters Patent is hereby corrected as shown below:

In the Claims

Column 59, Line 14, Claim 1, delete "di($C_{1-4}$alkyl)carbamyl," and insert -- di($C_{1-4}$ alkyl)carbamyl, --, therefor.

Column 59, Line 18, Claim 1, delete "di-$C_{1-4}$alkylamino sulfonyl," and insert -- di-$C_{1-4}$ alkylaminosulfonyl, --, therefor.

Column 59, Lines 19-20, Claim 1, delete "di-$C_{1-4}$alkylaminosulfonylamino;" and insert -- di-$C_{1-4}$ alkylaminosulfonylamino; --, therefor.

Column 59, Lines 22-23, Claim 1, delete "di($C_{1-4}$alkyl)carbamyl," and insert -- di($C_{1-4}$ alkyl)carbamyl, --, therefor.

Column 60, Line 7, Claim 8, delete "$C_{3-7}$cycloalkyl," and insert -- $C_{3-7}$ cycloalkyl, --, therefor.

Column 60, Line 10, Claim 8, delete "di($C_{1-4}$alkyl)carbamyl," and insert -- di($C_{1-4}$ alkyl)carbamyl, --, therefor.

Column 60, Lines 13-14 (approx.), Claim 8, delete "$C_{1-6}$alklaminosulfonyl, di-$C_{1-4}$ alklaminosulfonyl, aminosulfonylamino" and insert -- $C_{1-6}$ alkylaminosulfonyl, di-$C_{1-4}$ alkylaminosulfonyl, aminosulfonylamino, --, therefor.

Column 60, Lines 15-16 (approx.), Claim 8, delete "di-$C_{1-4}$alkylaminosulfonylamino;" and insert -- di-$C_{1-4}$ alkylaminosulfonylamino; --, therefor.

Column 60, Line 24, Claim 8, delete "alkylamino," and insert -- $C_{1-3}$ alkylamino, --, therefor.

Column 61, Line 16 (approx.), Claim 11, delete "thereof" and insert -- thereof; --, therefor.

Signed and Sealed this
Seventeenth Day of March, 2020

Andrei Iancu
*Director of the United States Patent and Trademark Office*

CERTIFICATE OF CORRECTION (continued)
U.S. Pat. No. 10,501,453 B2

Column 61, Line 19, Claim 11, delete "$C_{1-6}$haloalkyl," and insert -- $C_{1-6}$ haloalkyl, --, therefor.

Column 61, Lines 19-20, Claim 11, delete "$C_{3-7}$cycloalkyl," and insert -- $C_{3-7}$ cycloalkyl, --, therefor.

Column 61, Line 21, Claim 11, delete "$C_{1-6}$haloalkoxy," and insert -- $C_{1-6}$ haloalkoxy, --, therefor.

Column 61, Line 21, Claim 11, delete "$C_{1-6}$alkylamino," and insert -- $C_{1-6}$ alkylamino, di-$C_{1-4}$-alkylamino, --, therefor.

Column 61, Line 22, Claim 11, delete "$C_{1-6}$alkylcarbamyl, di($c_{1-4}$alkyl)carbamyl," and insert -- $C_{1-6}$ alkylcarbamyl, di($C_{1-4}$ alkyl)carbamyl, --, therefor.

Column 61, Lines 23-24 (approx.), Claim 11, delete "$C_{1-6}$alkoxycarbonyl, $C_{1-6}$alkylcarbonyloxy, $C_{1-6}$alkylsulfonyl, $C_{1-6}$alkylcarbonylamino," and insert -- $C_{1-6}$ alkoxycarbonyl, $C_{1-6}$ alkylcarbonyloxy, $C_{1-6}$ alkylsulfonyl, $C_{1-6}$ alkylcarbonylamino, --, therefor.

Column 61, Lines 25-26, Claim 11, delete "$C_{1-6}$alkylaminosulfonyl," and insert -- $C_{1-6}$ alkylaminosulfonyl, --, therefor.

Column 61, Line 27, Claim 11, delete "$C_{1-6}$alkylaminosulfonylamino," and insert -- $C_{1-6}$ alkylaminosulfonylamino, --, therefor.

Column 61, Line 29, Claim 11, delete "$C_{1-6}$haloalkyl," and insert -- $C_{1-6}$ haloalkyl, --, therefor.

Column 61, Lines 29-30, Claim 11, delete "$C_{3-7}$cycloalkyl," and insert -- $C_{3-7}$ cycloalkyl, --, therefor.

Column 61, Line 32, Claim 11, delete "$C_{1-6}$alkylcarbamyl, di($C_{1-4}$alkyl)carbamyl," and insert -- $C_{1-6}$ alkylcarbamyl, di($C_{1-4}$ alkyl)carbamyl, --, therefor.

Column 62, Lines 11-13, Claim 13, delete "5-(4 chlorophenyl)-N-(6-methoxybenzo[d]thiazol-2-yl)-1,3,4-oxadiazol-2-amine" and insert -- 5-(4-chlorophenyl)-N-(6-methoxybenzo[d]thiazol-2-yl)-1,3,4-oxadiazol-2-amine --, therefor.